(12) United States Patent
Hayakawa et al.

(10) Patent No.: US 10,584,193 B2
(45) Date of Patent: Mar. 10, 2020

(54) FLAT ELLIPTICAL POLYMER PARTICLES, AND USE THEREOF

(71) Applicant: Nisshinbo Holdings Inc., Tokyo (JP)

(72) Inventors: Kazutoshi Hayakawa, Chiba (JP); Toshifumi Hashiba, Chiba (JP); Erina Matsuzaka, Chiba (JP)

(73) Assignee: NISSHINBO HOLDINGS INC., Tokyo (JP)

( * ) Notice: Subject to any disclaimer, the term of this patent is extended or adjusted under 35 U.S.C. 154(b) by 23 days.

(21) Appl. No.: 15/571,919

(22) PCT Filed: May 2, 2016

(86) PCT No.: PCT/JP2016/063544
§ 371 (c)(1),
(2) Date: Nov. 6, 2017

(87) PCT Pub. No.: WO2016/181877
PCT Pub. Date: Nov. 17, 2016

(65) Prior Publication Data
US 2018/0134823 A1    May 17, 2018

(30) Foreign Application Priority Data
May 8, 2015   (JP) ................................ 2015-095705

(51) Int. Cl.
*B32B 5/16*   (2006.01)
*C08F 20/14*   (2006.01)
(Continued)

(52) U.S. Cl.
CPC ............ *C08F 20/14* (2013.01); *A61K 8/0245* (2013.01); *A61K 8/8152* (2013.01); *A61Q 1/00* (2013.01);
(Continued)

(58) Field of Classification Search
CPC ....................... C08F 2500/24; Y10T 428/2982
(Continued)

(56) References Cited

U.S. PATENT DOCUMENTS

| | | | |
|---|---|---|---|
| 5,559,202 A | 9/1996 | Yoshikawa | |
| 2008/0112886 A1* | 5/2008 | Mitragotri | ............ A61K 9/0097 424/9.1 |
| 2018/0118867 A1* | 5/2018 | Hayakawa | ............ C09D 129/04 |

FOREIGN PATENT DOCUMENTS

| | | |
|---|---|---|
| JP | 5-317688 A | 12/1993 |
| JP | 2000-38455 A | 2/2000 |

(Continued)

OTHER PUBLICATIONS

Shin & Kim, Preparation of spheroidal and ellipsoidal particles from spherical polymer particles by extension of polymer film, Colloid Polym Sci (2012) 290:1309-1315, DOI 10.1007/s00396-012-2656-4. (Year: 2012).*

(Continued)

*Primary Examiner* — Hoa (Holly) Le
(74) *Attorney, Agent, or Firm* — Westerman, Hattori, Daniels & Adrian, LLP

(57) ABSTRACT

These flat elliptical polymer particles have a front view, a planar view, and a side view in a projection diagram based on third-angle projection which are all elliptical. The flat elliptical polymer particles satisfy (1)-(4): (1) the average length ($L_{AV}$) of flat portions satisfies $0.13 \le (L_{AV}) \le 500$ μm; (2) the average breadth ($D_{AV}$) of the flat portions satisfies $0.1 \le (D_{AV}) \le 250$ μm; (3) the average ($P1_{AV}$) aspect ratio (L/D) calculated from the length (L) and the breadth (D) satisfies $1.3 < P1_{AV} \le 50$; and (4) the average ($P2_{AV}$) aspect ratio (D/T) calculated from the breadth (D) and the thickness (T) of the side surface satisfies $1.2 < P2_{AV} \le 100$.

24 Claims, 3 Drawing Sheets

Figure 1:

(51) Int. Cl.
| | |
|---|---|
| C09J 11/08 | (2006.01) |
| C09D 201/00 | (2006.01) |
| C09J 201/00 | (2006.01) |
| A61Q 19/00 | (2006.01) |
| C08F 212/08 | (2006.01) |
| C08F 220/14 | (2006.01) |
| A61Q 1/02 | (2006.01) |
| C08F 120/14 | (2006.01) |
| C08F 2/22 | (2006.01) |
| C08F 2/30 | (2006.01) |
| C09D 7/65 | (2018.01) |
| C09D 7/40 | (2018.01) |
| A61K 8/02 | (2006.01) |
| A61K 8/81 | (2006.01) |
| A61Q 1/00 | (2006.01) |
| A61Q 19/10 | (2006.01) |
| C08F 12/08 | (2006.01) |
| C09D 11/107 | (2014.01) |
| C09D 11/108 | (2014.01) |
| C09D 125/14 | (2006.01) |
| C09D 133/12 | (2006.01) |
| C09J 125/14 | (2006.01) |
| C09J 133/12 | (2006.01) |
| G02B 5/02 | (2006.01) |

(52) U.S. Cl.
CPC ............... *A61Q 1/02* (2013.01); *A61Q 19/00* (2013.01); *A61Q 19/10* (2013.01); *C08F 2/22* (2013.01); *C08F 2/30* (2013.01); *C08F 12/08* (2013.01); *C08F 120/14* (2013.01); *C08F 212/08* (2013.01); *C08F 220/14* (2013.01); *C09D 7/65* (2018.01); *C09D 7/69* (2018.01); *C09D 7/70* (2018.01); *C09D 11/107* (2013.01); *C09D 11/108* (2013.01); *C09D 125/14* (2013.01); *C09D 133/12* (2013.01); *C09D 201/00* (2013.01); *C09J 11/08* (2013.01); *C09J 125/14* (2013.01); *C09J 133/12* (2013.01); *C09J 201/00* (2013.01); *G02B 5/0242* (2013.01); *A61K 2800/28* (2013.01); *A61K 2800/41* (2013.01); *A61K 2800/412* (2013.01); *A61K 2800/60* (2013.01); *C08F 2500/24* (2013.01)

(58) Field of Classification Search
USPC ...................................................... 428/402
See application file for complete search history.

(56) References Cited

FOREIGN PATENT DOCUMENTS

| | | |
|---|---|---|
| JP | 2007-256151 A | 10/2007 |
| JP | 2009-235353 A | 10/2009 |
| JP | 2009-235355 A | 10/2009 |

OTHER PUBLICATIONS

Wang et al., Morphology-controlled two-dimensional elliptical hemisphere arrays fabricated by a colloidal crystal based micromolding method, J. Mater. Chem., 2010, 20, 152-158. (Year: 2010).*

Dugyala et al., "Shape anisotropic colloids: synthesis, packing behavior, evaporation driven assembly, and their application in emulsion stabilization", Soft Matter, 2013, 9, 6711 (Year: 2013).*

International Search Report dated Aug. 2, 2016, issued in counterpart International Application No. PCT/JP2016/063544 (2 pages).

Champion J.A. et al., "Making polymeric micro- and nanoparticles of complex shapes", Proceedings of the National Academy of Sciences, Jul. 17, 2007, vol. 104, No. 29, pp. 11901-11904; cited in Extended (supplementary) European Search Report dated Nov. 15, 2018.

Heslinga, M.J. et al., "Fabrication of biodegradable spheroidal microparticles for drug delivery applications", Journal of Controlled Release, Elsevier, Sep. 15, 2009, vol. 138, No. 3, pp. 235-242; cited in Extended (supplementary) European Search Report dated Nov. 15, 2018.

Extended (supplementary) European Search Report dated Nov. 15, 2018, issued in counterpart European Application No. 16792602.1. (11 pages).

* cited by examiner

— OPTICAL SHEET 3 (POLYMER PARTICLE A3)
--- OPTICAL SHEET 7 (POLYMER PARTICLE B1)
…… OPTICAL SHEET 9 (POLYMER PARTICLE B3)

FLAT ELLIPTICAL POLYMER PARTICLES, AND USE THEREOF

TECHNICAL FIELD

The present invention relates to flat elliptical polymer particles, and to uses thereof.

BACKGROUND ART

Micron-size polymer particles and inorganic particles are used as fillers and specimens in diverse fields, such as electrical and electronic materials, optical materials, paints, inks, construction materials, biological and pharmaceutical materials, and cosmetics.

In particular, particles of unusual, non-spherical shapes are capable of exhibiting various properties differing from those of spherical particles in terms of, for example, optical characteristics and tactile feel. Such particles have thus been the subject of active development efforts in recent years, and new applications are constantly emerging.

The inventors have worked thus far on the development of elliptical or needle-shaped polymer particles of high aspect ratio, and have discovered a variety of particles with characteristics superior to those of conventional spherical particles in terms of such properties as hiding power, light-diffusing ability and tactile qualities (Patent Documents 1 and 2). However, in this technical field, novel polymer particles continue to be developed in an effort to achieve still further improvements in characteristics.

PRIOR ART DOCUMENTS

Patent Documents

Patent Document 1: JP-A 2009-235353
Patent Document 2: JP-A 2009-235355

SUMMARY OF THE INVENTION

Problems to be Solved by the Invention

It is therefore an object of the present invention to provide a novel flat elliptical polymer particle.

Means for Solving the Problems

The inventors have conducted extensive investigations aimed at achieving the above object. As a result, they have discovered that, by improving the art of synthesizing elliptical polymer particles, flat elliptical polymer particles in which the plane of the minor axis of an elliptical particle is flattened can be obtained, and that such flat elliptical polymer particles have distinctive characteristics differing from those of conventional particles in terms of, for example, light-diffusing ability, UV-cutting ability, tactile qualities and flowability.

Accordingly, the invention provides:
1. A flat elliptical polymer particle which has, in projections based on the third-angle projection method, a front view, a plan view and a side view that are all elliptical and which satisfies conditions (1) to (4) below:
   (1) a flat region of the particle has an average length $L_{AV}$ such that $0.13 \leq L_{AV} \leq 500$ μm,
   (2) a flat region of the particle has an average breadth $D_{AV}$ such that $0.1 \leq D_{AV} \leq 250$ μm,
   (3) the aspect ratio L/D calculated from the length L and breadth D has an average value $P1_{AV}$ such that $1.3 < P1_{AV} \leq 50$, and
   (4) the aspect ratio D/T calculated from the breadth D and a lateral face thickness T has an average value $P2_{AV}$ such that $1.2 < P2_{AV} \leq 100$;
2. The flat elliptical polymer particle of 1 above which is obtained by solution polymerization (exclusive of seed polymerization);
3. The flat elliptical polymer particle of 1 or 2 above which further satisfies condition (5) below:
   (5) the aspect ratio L/T calculated from the length L and the thickness T has an average value $P3_{AV}$ such that $1.56 < P3_{AV} \leq 150$;
4. The flat elliptical polymer particle of any of 1 to 3 above which comprises, attached to or included within at least a surface or a surface layer portion thereof, a fine particle that satisfies condition (6) below:
   (6) the fine particle attached to or included within the particle surface or surface layer portion has a particle size SP such that $1/1,000 \times D_{AV} \leq SP \leq 1/2 \times D_{AV}$;
5. The flat elliptical polymer particle of 4 above which has an uneven surface shape owing to the fine particle;
6. The flat elliptical polymer particle of any of 1 to 5 above, wherein the ratio SB/SD between the actual specific surface area SB of the flat elliptical polymer particle and the theoretical specific surface area SD of a spherical particle calculated from the volume mean particle size of the flat elliptical polymer particle satisfies the condition $SB/SD \geq 1.2$;
7. The flat elliptical polymer particle of any of 1 to 6 above which has a bulk density of from 0.01 to 0.7 g/mL;
8. The flat elliptical polymer particle of any of 1 to 7 above which has a water absorption of at least 60 mL per 100 g of particles and/or an oil absorption of at least 60 mL per 100 g of particles;
9. The flat elliptical polymer particle of any of 1 to 8 above which is a crosslinked polymer particle;
10. The flat elliptical polymer particle of 9 above which has a heat resistance of at least 100° C.;
11. A method for producing the flat elliptical polymer particle of any of 1 to 10 above by solution polymerizing an unsaturated monomer in a solvent and in the presence of a polymerization initiator, wherein the solvent is a mixed solvent of water, a hydrophilic organic solvent and a hydrophobic organic solvent, and
    the polymerization initiator is used as one type that dissolves in at least one of the water, the hydrophilic organic solvent and the hydrophobic organic solvent, or is used as a combination of two or more types that dissolves in each of the water, the hydrophilic organic solvent and the hydrophobic organic solvent;
12. The flat elliptical polymer particle production method of 11 above, wherein the unsaturated monomer is at least one selected from the group consisting of styrenic monomers, (meth)acrylic acids, (meth)acrylic ester monomers and vinyl ester monomers;
13. The flat elliptical polymer particle production method of 11 or 12 above, wherein the unsaturated monomer includes an unsaturated monomer that is liquid at 25° C. and hydrophobic, and
    the ratio of hydrophobic liquid ingredients, including the hydrophobic liquid unsaturated monomer and the hydrophobic organic solvent, relative to the total weight of charged ingredients, is set to at least 10 wt %;
14. The flat elliptical polymer particle production method of any of 11 to 13 above, wherein the polymerization initiator is a combination of at least one type of water-soluble initiator and at least one type of oil-soluble initiator;
15. The flat elliptical polymer particle production method of any of 11 to 14 above, wherein the hydrophobic organic solvent is an organic compound having a molecular weight of at least 200;
16. The flat elliptical polymer particle production method of any of 13 to 15 above, wherein the hydrophobic organic solvent has an ability to dissolve the hydrophobic liquid unsaturated monomer and does not have an ability to dissolve flat elliptical polymer particles that form in the polymerization reaction;
17. A resin composition obtained using the flat elliptical polymer particle of any of 1 to 10 above;
18. A light-diffusing sheet obtained using the flat elliptical polymer particle of any of 1 to 10 above;
19. A paint composition obtained using the flat elliptical polymer particle of any of 1 to 10 above;
20. An ink composition obtained using the flat elliptical polymer particle of any of 1 to 10 above;
21. A cosmetic preparation obtained using the flat elliptical polymer particle of any of 1 to 10 above;
22. A material for the electrical or electronics industry obtained using the flat elliptical polymer particle of any of 1 to 10 above;
23. An adhesive obtained using the flat elliptical polymer particle of any of 1 to 10 above;
24. A thermally cavitated product having pores obtained using the flat elliptical polymer particle of any of 1 to 10 above;
25. A diagnostic agent for medical use obtained using the flat elliptical polymer particle of any of 1 to 10 above; and
26. A flat elliptical polymer particle obtained by solution polymerization (exclusive of seed polymerization).

Advantageous Effects of the Invention

The present invention provides a novel micron-size flat elliptical polymer particle. This flat elliptical polymer particle can be obtained in one step by solution polymerization without using seed particles. The production method is simpler than production methods which include a particle compression/transfer step and solution polymerization using seed particles, and also has the advantage that bulk production at one time is possible. Moreover, compared with production methods that carry out physical cutting and the like, the particles have no end faces or sharp edges. Nor is there a need for preforming or for a step to uniformly shape the particles using a mold.

The flat elliptical polymer particle of the invention, because it has a flat shape while maintaining the properties of ellipsoidal polymer particles, has distinctive characteristics in terms of light-diffusing ability, UV-cutting ability, tactile qualities and flowability, and can be suitably used as an additive in cosmetics, paints, inks, film sheets, and molded or formed articles.

BRIEF DESCRIPTION OF THE DIAGRAMS

Figure 2:
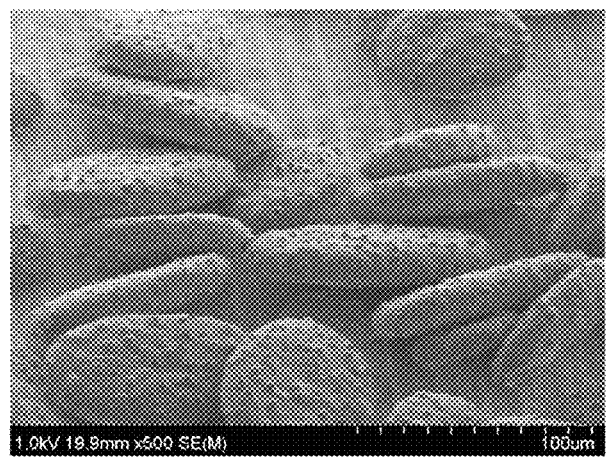
Figure 3:
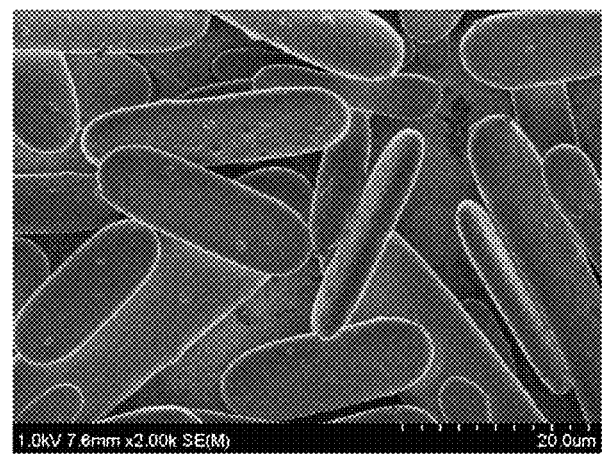
Figure 4:
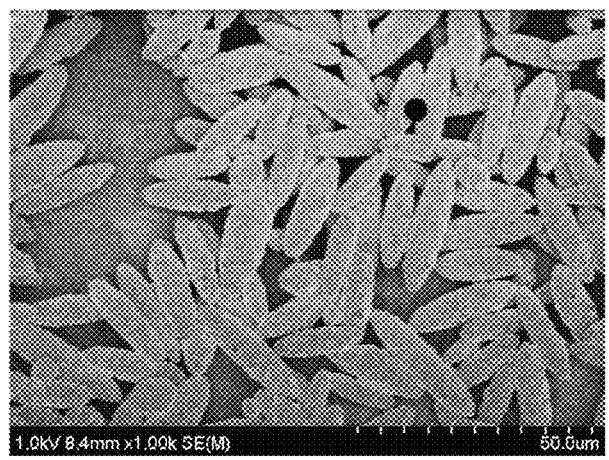
Figure 5:
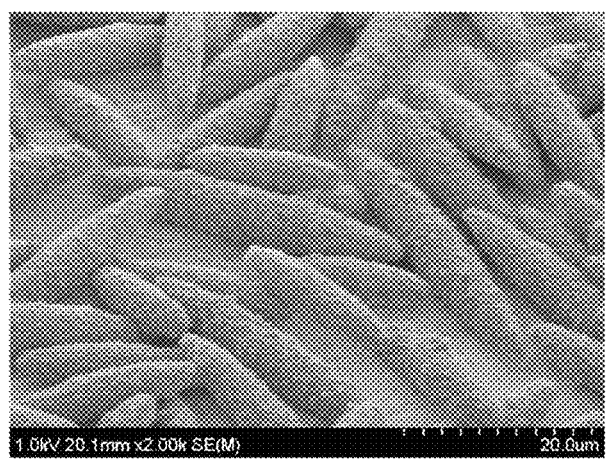
Figure 6:
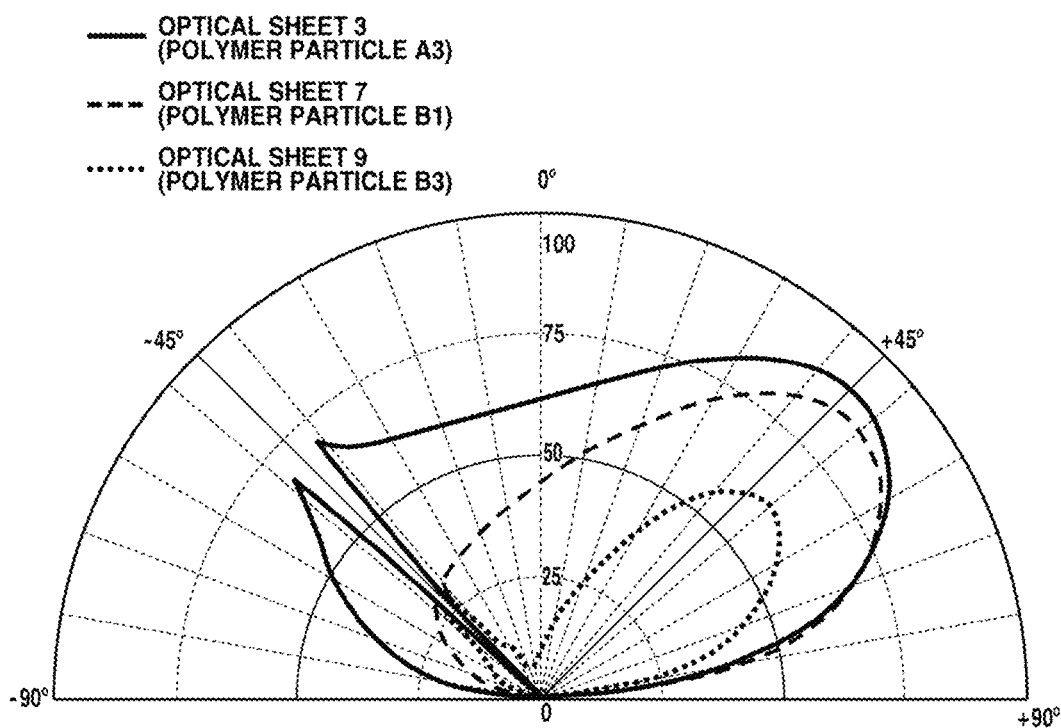
Figure 7:
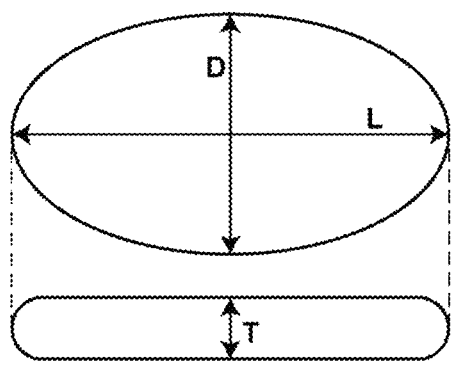

FIG. 1 shows a scanning electron micrograph (300×) of particles obtained in Working Example 1-1.
FIG. 2 shows a scanning electron micrograph (500×) of the same particles taken obliquely at an angle of 45°.
FIG. 3 shows a scanning electron micrograph (2,000×) of particles obtained in Working Example 1-5.
FIG. 4 shows a scanning electron micrograph (1,000×) of particles obtained in Comparative Example 1-1.
FIG. 5 shows a scanning electron micrograph (2,000×) of the same particles taken obliquely at an angle of 45°.
FIG. 6 is a diagram showing the light scattering distribution of reflected light obtained with an automated goniophotometer for Optical Sheets 3, 7 and 9 produced using Polymer Particles A3, B1 and B3.
FIG. 7 is a diagram showing the length L, breadth D and thickness T of the flat elliptical polymer particle of the invention.

EMBODIMENT FOR CARRYING OUT THE INVENTION

[Flat Elliptical Polymer Particle]
The flat elliptical polymer particle of the invention has, in projections based on the third-angle projection method, a front view, a plan view and a side view that are all elliptical and satisfies conditions (1) to (4) below:
(1) a flat region of the particle has an average length $L_{AV}$ such that $0.13 \leq L_{AV} \leq 500$ μm,
(2) a flat region of the particle has an average breadth $D_{AV}$ such that $0.1 \leq D_{AV} \leq 250$ μm,
(3) the aspect ratio L/D calculated from the length L and breadth D has an average value $P1_{AV}$ such that $1.3 < P1_{AV} \leq 50$, and
(4) the aspect ratio D/T calculated from the breadth D and a lateral face thickness T has an average value $P2_{AV}$ such that $1.2 < P2_{AV} \leq 100$.
The length L, breadth D and thickness T are depicted in FIG. 6.

In this invention, a "flat elliptical" shape is not limited only to shapes obtained by flattening a mathematically defined ellipsoid, but encompasses also particles of ellipsoidal shapes having a flat region, including flat ellipsoidal shapes such as flat rectangular shapes with rounded corners and flat oval shapes.

In the present invention, the average length $L_{AV}$ of the flat region is preferably such that $1 \leq L_{AV} \leq 300$ μm, more preferably such that $3 \leq L_{AV} \leq 150$ μm, and even more preferably such that $5 \leq L_{AV} \leq 80$ μm.

The average breadth $D_{AV}$ of the flat region is preferably such that $0.1 \leq D_{AV} \leq 150$ μm, more preferably such that $0.5 \leq D_{AV} \leq 100$ μm, and even more preferably such that $1 \leq D_{AV} \leq 50$ μm.

The aspect ratio L/D calculated from the length L and breadth D has an average value $P1_{AV}$ which is preferably such that $1.5 \leq P1_{AV} \leq 30$, more preferably such that $1.8 \leq P1_{AV} \leq 30$, and even more preferably such that $2 \leq P1_{AV} \leq 20$.

The aspect ratio D/T calculated from the breadth D and lateral face thickness T has an average value $P2_{AV}$ which is preferably such that $1.3 \leq P2_{AV} \leq 50$, more preferably such that $1.5 \leq P2_{AV} \leq 30$, and even more preferably such that $2 \leq P2_{AV} \leq 20$.

Given that a larger surface area of contact between the particle and a solid surface increases the adhesive strength of the particle and that a smaller resistance to fluids is less likely to result in the release or shedding of particles, the flat elliptical polymer particle of the invention preferably has a shape that also satisfies condition (5) below:
(5) the aspect ratio L/T calculated from the length L and the thickness T has an average value $P3_{AV}$ such that $1.56 < P3_{AV} \leq 150$.

The average value $P3_{AV}$ of the aspect ratio L/T is preferably such that $1.7 \leq P3_{AV} \leq 100$, more preferably such that $2 \leq P3_{AV} \leq 50$, and even more preferably such that $3 \leq P3_{AV} \leq 30$.

The flat elliptical polymer particle of the invention preferably possesses at least one of the following characteristics: fine irregularities at the particle surface, a high porosity, or a relatively large specific surface area. It is preferable in particular for the particle to be porous or to have attached to or included within at least a surface or a surface layer portion thereof a fine particle that satisfies condition (6) below. The flat elliptical polymer particle of the invention more preferably has an uneven surface shape owing to such a fine particle.

(6) The fine particle attached to or included within the particle surface or surface layer portion has a particle size SP such that $1/1{,}000 \times D_{AV} \leq SP \leq 1/2 \times D_{AV}$.

This particle size SP is more preferably such that $1/100 \times D_{AV} \leq SP \leq 1/2 \times D_{AV}$ and even more preferably such that $1/20 \times D_{AV} \leq SP \leq 1/2 \times D_{AV}$.

The fine particle is preferably composed of the same ingredients as the flat elliptical polymer particle, and is preferably attached to or included within the surface or surface layer portion of the flat elliptical polymer particle.

The flat elliptical polymer particle of the invention has a ratio SB/SD between the actual specific surface area SB of the flat elliptical polymer particle and the theoretical specific surface area SD of a spherical particle calculated from the volume mean particle size of the flat elliptical polymer particle which preferably satisfies the condition $SB/SD \geq 1.2$, more preferably satisfies the condition $SB/SD \geq 1.5$, even more preferably satisfies the condition $SB/SD \geq 1.8$, and most preferably satisfies the condition $SB/SD \geq 2.0$.

The actual specific surface area SB of the flat elliptical polymer particle of the invention, although not particularly limited, is preferably from 0.1 to 30 $m^2/g$, more preferably from 0.5 to 20 $m^2/g$, and even more preferably from 1 to 10 $m^2/g$. The specific surface area SB is a value measured by the nitrogen gas adsorption method.

The flat elliptical polymer particle of the invention has a bulk density of preferably from 0.01 to 0.7 g/mL, more preferably from 0.05 to 0.65 g/mL, and even more preferably from 0.1 to 0.6 g/mL.

Also, the flat elliptical polymer particle preferably has an affinity for at least aqueous systems or oil systems, and more preferably has an affinity to both.

Specifically, it is preferable for the water absorption to be at least 60 mL per 100 g of particles and/or the oil absorption to be at least 60 mL per 100 g of particles, and more preferable for the water absorption to be at least 60 mL per 100 g of particles and the oil absorption to be at least 60 mL per 100 g of particles.

Both the water absorption and the oil absorption are more preferably at least 80 mL per 100 g of particles, even more preferably at least 100 mL per 100 g of particles, and most preferably at least 120 mL per 100 g of particles.

Moreover, the flat elliptical polymer particle, from the standpoint of increasing its heat resistance and chemical resistance, is preferably a crosslinked polymer particle.

The crosslinking method is not particularly limited, although in the subsequently described method for producing flat elliptical polymer particles, crosslinked polymer particles can be obtained by carrying out the polymerization reaction using a polyfunctional monomer that contributes as a crosslinking agent.

By having the polymer be crosslinked, the resulting polymer particles are endowed with an excellent heat resistance such that, when 0.5 g of the polymer particles of the invention are heated for two hours at 100° C., they maintain their initial shape (heat resistance is at least 100° C.).

The material making up the flat elliptical polymer particle of the invention is not particularly limited, provided it can be obtained using a solution-polymerizable monomer. For example, the material is preferably composed of at least one selected from among styrene resins, (meth)acrylic resins, vinyl carboxylate resins, poly-N-vinyl compound-based resins, polyolefin resins, polydiene resins, polyester resins, silicone resins, polyurethane resins, polyamide resins, polyimide resins, epoxy resins, polyvinyl butyral resins, phenolic resins, amino resins, oxazoline resins and carbodiimide resins. These resins may be either homopolymers or copolymers. For example, "styrene resins" are resins that use a styrene compound as the main constituent unit, and include not only homopolymers of styrene compounds, but also copolymers of styrene compounds or of a styrene compound and another monomer.

Exemplary styrene resins include (co)polymers of styrene compounds, and copolymers of styrene and an olefin or a conjugated diene, such as styrene-(meth)acrylic acid copolymers, styrene-(meth)acrylic ester copolymers, acrylonitrile-styrene copolymers, acrylonitrile-chlorinated polyethylene-styrene copolymers, styrene-maleic anhydride copolymers or modified forms thereof, styrene-butadiene block copolymers (SBR), styrene-butadiene-styrene block copolymers (SBS), hydrogenated styrene-butadiene-styrene block copolymers (SEBS), styrene-isoprene block copolymers (SIR), styrene-isoprene-styrene block copolymers (SIS) and hydrogenated styrene-isoprene-styrene block copolymers (SEPS).

Exemplary (meth)acrylic resins include (meth)acrylic acid (co)polymers, (meth)acrylic ester (co)polymers, (meth)acrylic acid-(meth)acrylic ester copolymers, vinyl ester-(meth)acrylic acid copolymers, vinyl ester-(meth)acrylic ester copolymers, olefin-(meth)acrylic acid copolymers such as ethylene-acrylic acid copolymers, olefin-(meth)acrylic ester copolymers such as ethylene-acrylic ester copolymers, N-vinyl compound-(meth)acrylic acid copolymers, N-vinyl compound-(meth)acrylic ester copolymers, conjugated diene-(meth)acrylic acid copolymers and conjugated diene-(meth)acrylic ester copolymers.

Exemplary vinyl carboxylate resins include (co)polymers of vinyl carboxylates, olefin-vinyl carboxylate copolymers such as ethylene-vinyl acetate copolymers, and vinyl carboxylate-conjugated diene copolymers. Exemplary poly-N-vinyl compound-based resins include (co)polymers of N-vinyl compounds, olefin-N-vinyl compound copolymers and conjugated diene-N-vinyl compound copolymers. Exemplary polyolefin resins include polyolefins, polyfluorinated olefins, copolymers of olefins and/or fluorinated polyolefins, and olefin-conjugated diene copolymers. Exemplary polydiene resins include (co)polymers of conjugated dienes.

Two or more resins made of unsaturated monomers, such as the above styrene resins, (meth)acrylic resins, vinyl carboxylate resins, poly-N-vinyl compound-based resins, polyolefin resins and polydiene resins, may be formed into a copolymer in accordance with the intended use and purpose.

Exemplary polyester resins include, without particular limitation, polyester resins made of an acid component that is primarily terephthalic acid or dimethyl terephthalate, and a glycol component that is primarily at least one alkylene glycol selected from among ethylene glycol, diethylene glycol, trimethylene glycol and butylene glycol; and polylactic acid.

Specific examples include polyethylene terephthalate, polyethylene naphthalate, polybutylene terephthalate, polybutylene naphthalate, polytrimethylene terephthalate, polycyclohexylenedimethylene terephthalate, polycyclohexylenedimethylene naphthalate, polybutylene terephthalate, polybutylene naphthalate and polylactic acid.

Exemplary silicone resins include, without particular limitation, those containing silicon-silicon bonds, silicon-carbon bonds, siloxane bonds or silicon-nitrogen bonds on the molecular chain.

Illustrative examples include polysiloxane, polycarbosilane and polysilazane.

Exemplary polyurethane resins include polyurethane resins obtained by polymerizing a polyol and a polyisocyanate.

Examples of the polyol in this case include ethylene glycol, diethylene glycol, propylene glycol, dipropylene glycol, glycerol, 1,1,1-trimethylolpropane, 1,2,5-hexanetriol, 1,3-butanediol, 1,4-butanediol, 4,4'-dihydroxyphenylpropane, 4,4'-dihydroxyphenylmethane and pentaerythritol.

Examples of the polyisocyanate include 4-tolylene diisocyanate, 2,6-tolylene diisocyanate, 4,4'-diphenylmethane diisocyanate, 2,4'-diphenylmethane diisocyanate, p-phenylene diisocyanate, isophorone diisocyanate and xylylene diisocyanate.

Examples of polyamide resins include polyamide resins obtained by polycondensing a dicarboxylic acid such as adipic acid, heptanedicarboxylic acid, octanedicarboxylic acid, nonanedicarboxylic acid, undecanedicarboxylic acid or dodecanedicarboxylic acid with a diamine such as tetramethylenediamine, hexamethylene diamine, octamethylenediamine, nonamethylenediamine, undecamethylenediamine or dodecamethylenediamine.

Additional examples include polyamide resins obtained by the ring-opening polymerization of a lactam such as α-pyrrolidone, ε-caprolactam, ω-laurolactam or ε-enantholactam.

Specific examples include nylon-6, nylon-11, nylon-12, nylon-6,6 and nylon-6,T.

Examples of polyimide resins include polyimide resins obtained by polymerizing a diamine such as o-phenylenediamine, m-phenylenediamine, p-phenylenediamine, 4,4'-diaminodiphenyl ether, 1,4-bis(aminomethyl)cyclohexane, 1,3-bis(aminomethyl)cyclohexane, 1,3-propanediamine, 1,4-butanediamine, 1,5-pentanediamine or 1,6-hexanediamine with a tetracarboxylic dianhydride such as 4,4'-hexafluoropropylidenebisphthalic dianhydride, 4,4'-biphthalic anhydride, diphenyl-2,3,3',4'-tetracarboxylic dianhydride, diphenyl-2,2',3,3'-tetracarboxylic dianhydride or pyromellitic dianhydride.

Exemplary epoxy resins include polyepoxides, aromatic polyepoxy compounds, glycidyl ethers of polyhydric phenols, glycidyl esters of polyhydric phenols, glycidyl aromatic polyamines, alicyclic polyepoxy compounds, aliphatic polyepoxy compounds and polyglycidyl esters of polyunsaturated fatty acids. Of these, aliphatic polyepoxy compounds and aromatic polyepoxy compounds are preferred.

Examples of polyvinyl butyral resins include the reaction product of polyvinyl alcohol and butyraldehyde, and the products obtained by crosslinking between the molecules with monobutyral bonds.

Examples of phenolic resins include resins obtained using organic compounds belonging to the phenols, such as phenol and cresol.

Examples of amino resins include urea resins, melamine resins and guanamine resins.

Examples of oxazoline resins include bisoxazoline compounds and compounds having a terminal oxazoline group that are obtained by reacting two chemical equivalents of oxazoline groups on a bisoxazoline compound with one chemical equivalent of carboxyl groups on a polybasic carboxylic acid. The oxazoline compound may be a polymer having at least two oxazoline groups per molecule obtained from a polymer by, for example, addition polymerization without ring opening of the oxazoline rings. Other exemplary oxazoline group-containing compounds include copolymers of an addition polymerizable oxazoline compound and a copolymerizable monomer that does not react with oxazoline groups.

Examples of carbodiimide resins include resins having at least one carbodiimide group that are obtained using one, two or more isocyanate compounds as the starting material.

Of these, the material of the flat elliptical polymer particle is more preferably a styrene resin, a (meth)acrylic resin, a vinyl carboxylate resin, a poly-N-vinyl compound-based resin, a polyolefin resin, a polydiene resin, a polyester resin, a silicone resin or a polyamide resin.

In particular, the flat elliptical polymer particle of the invention is preferably a (co)polymer obtained using at least one type of monomer selected from among styrene compounds, (meth)acrylic acids, (meth)acrylic esters, vinyl esters, N-vinyl compounds, olefins, fluorinated olefins and conjugated dienes; and more preferably a (co)polymer containing, as essential units, recurring units obtained from at least one monomer selected from among styrene compounds, (meth)acrylic acids and (meth)acrylic esters.

Illustrative examples include preferably polystyrene, styrene-(meth)acrylic acid copolymers, styrene-(meth)acrylic ester copolymers, poly(meth)acrylic acids, polymethyl (meth)acrylate, polyethyl (meth)acrylate, polybutyl (meth)acrylate, (meth)acrylic acid-methyl (meth)acrylate copolymers, (meth)acrylic ester copolymers, polyvinyl acetate, poly-N-vinylpyrrole, poly-N-vinylcarbazole, poly-N-vinylindole, poly-N-vinylpyrrolidone, polyethylene, polypropylene, polyvinyl fluoride, polytetrafluoroethylene, polybutadiene, polyisoprene and copolymers thereof; and more preferably polystyrene, styrene-(meth)acrylic acid copolymers, styrene-(meth)acrylic ester copolymers, poly(meth)acrylic acid, polymethyl (meth)acrylate, polyethyl (meth)acrylate, polybutyl (meth)acrylate, (meth)acrylic acid-methyl (meth)acrylate copolymers and (meth)acrylic ester copolymers.

As mentioned above, the resin may be a suitable cured copolymer obtained using a polyfunctional crosslinking agent.

The flat elliptical polymer particle of the invention may be a mixture of two or more types, so long as it satisfies above conditions (1) to (4).

[Method for Producing Flat Elliptical Polymer Particles]

Because the flat elliptical polymer particle of the invention can be produced in one step by solution polymerization, and can be produced by a batch process that does not include a particle compression/transfer step, bulk production at one time without passing through a plurality of steps is possible.

Solution polymerization in this invention is defined as a polymerization process that causes a polymerization reaction to proceed in a medium containing at least a monomer and a polymerization initiator, and causes polymer particles to separate out or form.

Examples of solution polymerization processes include suspension polymerization, emulsion polymerization, dispersion polymerization and seed polymerization, as well as combined processes based on these.

Suspension polymerization is a process in which a monomer and agents such as a polymerization initiator that are soluble in the monomer are mechanically agitated in a medium in which these do not readily dissolve, causing the polymerization reaction to proceed in a suspended state and causing polymer particles to separate out or form.

Emulsion polymerization is a process in which a medium such as water is mixed with a monomer and agents such as an emulsifying agent (surfactant) that are poorly soluble in the medium, along with which a polymerization initiator soluble in the medium is added, causing the polymerization reaction to proceed and polymer particles to separate out or form.

Dispersion polymerization is a process in which the polymerization reaction is made to proceed in a uniform solution of monomer, initiator, dispersion stabilizer and the like dissolved in a liquid medium within which the monomer dissolves but becomes insoluble with polymerization, causing polymer particles to separate out or form.

Seed polymerization is a polymerization process in which other particles serving as seeds are added beforehand at the time of polymerization and the polymerization reactions is carried out at the surface of these particles.

Flat elliptical particles can be obtained by these various types of solution polymerization, although the flat elliptical polymer particles of the invention are produced by solution polymerization exclusive of seed polymerization; that is, by suspension polymerization, emulsion polymerization, dispersion polymerization or a combination thereof. With these methods, the seed particle preparation step required in seed polymerization can be omitted.

In this invention, by varying the types and weight ratios of the monomer, polymerization initiator and solvent in these methods, and also the ingredients and weight ratios of the dispersant and the emulsifying agent, the target flat elliptical polymer particles can be prepared.

In particular, to efficiently obtain flat elliptical polymer particles, it is preferable to use a mixed solvent containing three types of solvent: water, a hydrophilic organic solvent, and a hydrophobic organic solvent.

No particular limitation is imposed on the proportions in which the water, hydrophilic organic solvent and hydrophobic organic solvent are used. However, from the standpoint of efficiently obtaining flat elliptical polymer particles, the weight ratio of water to hydrophilic organic solvent to hydrophobic organic solvent is preferably from 98:1:1 to 30:30:40, more preferably from 96:2:2 to 40:25:35, and even more preferably from 93:2:5 to 50:20:30.

In particular, the hydrophilic organic solvent and the hydrophobic organic solvent are used in proportions which preferably satisfy the condition
hydrophilic organic solvent≤hydrophobic organic solvent,
and more preferably satisfy the condition
hydrophilic organic solvent≤hydrophobic organic solvent.

It is preferable to select a hydrophilic organic solvent and a hydrophobic organic solvent which are miscible (compatible).

In addition, it is preferable to select a solvent such that the monomer serving as the chief ingredient (more than 50 wt %) of the monomers used in polymerization dissolves in at least the hydrophilic organic solvent or the hydrophobic organic solvent.

In this invention, "hydrophilic organic solvent" refers to a solvent which maintains a uniform appearance as a mixed solvent with an equal volume of water. Also, "hydrophobic organic solvent" refers to a solvent which, when gently mixed with an equal volume of pure water at one atmosphere $(1.013 \times 10^5$ Pa) and a temperature of 20° C., results in a mixed liquid that cannot maintain a uniform appearance after flow has subsided.

Examples of the water include tap water, deionized water and distilled water.

Examples of hydrophilic organic solvents include methanol, ethanol, 1-propanol, 2-propanol, ethylene glycol, propylene glycol, butylene glycol, dipropylene glycol, methyl cellosolve, ethyl cellosolve, propyl cellosolve, methyl cellosolve acetate, ethyl cellosolve acetate, methyl carbitol, ethyl carbitol, butyl carbitol, ethyl carbitol acetate, acetone, tetrahydrofuran, dimethyl formamide, N-methyl-2-pyrrolidone and acetonitrile. These may be used singly or two or more may be used in admixture.

Examples of hydrophobic organic solvents include higher alcohols such as 1-butanol, 2-butanol, isobutanol, tert-butanol, 1-pentanol, 2-pentanol, 3-pentanol, 2-methyl-1-butanol, isopentyl alcohol, tert-pentyl alcohol, 1-hexanol, 2-methyl-1-pentanol, 4-methyl-2-pentanol, 2-ethylbutanol, 1-heptanol, 2-heptanol, 3-heptanol, 2-octanol, 2-ethyl-1-hexanol, benzyl alcohol and cyclohexanol; ether alcohols such as butyl cellosolve; polyethers such as polypropylene glycol and polybutylene glycol; ketones such as methyl ethyl ketone, methyl isobutyl ketone and cyclohexanone; esters such as ethyl acetate, butyl acetate, ethyl propionate and butyl carbitol acetate; aliphatic or aromatic hydrocarbons such as pentane, 2-methylbutane, n-hexane, cyclohexane, 2-methylpentane, 2,2-dimethylbutane, 2,3-dimethylbutane, heptane, n-octane, isooctane, 2,2,3-trimethylpentane, decane, nonane, cyclopentane, methyl cyclopentane, methyl cyclohexane, ethyl cyclohexane, p-menthane, dicyclohexyl, benzene, toluene, xylene, ethylbenzene, liquid paraffin, mineral oil and heat transfer medium oils; siloxane compounds such as polydimethylsiloxane, polymethylphenylsiloxane, polydiphenylsiloxane and silicone oils; and halogenated hydrocarbons such as carbon tetrachloride, trichloroethylene, chlorobenzene and tetrabromoethane. These hydrophobic organic solvents may include modified compounds and copolymers and other modified polymer compounds that are substituted with carbon, nitrogen, oxygen, hydrogen, halogen or the like, within a range that does detract from the advantageous effects of the invention. Such hydrophobic organic solvents may be used singly or two or more may be used in combination.

In particular, it is preferable for the hydrophobic organic solvent used to be a hydrophobic organic solvent which has 8 or more carbon atoms and does not react with the starting monomer under the polymerization conditions. By having such a hydrophobic organic solvent be present within the reaction system, the dispersibility of the polymer particles as they form can be enhanced, making more uniform control of the particle size possible.

The organic compound having 8 or more carbon atoms is not particularly limited, provided that it is a solid or liquid at room temperature, is compatible with the hydrophilic organic solvent to be used and does not have an adverse influence on the polymerization reaction. However, taking into consideration such factors as the polymerization reaction temperature, an organic compound having a melting point of 80° C. or less is preferred, one having a melting point of 60° C. or less is more preferred, one having a melting point of 40° C. or less is even more preferred, and one having a melting point of 30° C. or less is best.

Such organic compounds are exemplified by hydrocarbon compounds, siloxane compounds and polyalkylene oxide group-containing compounds. The number of carbon atoms should be 8 or more, although taking into consideration the dispersion stability of the particles to be obtained, the number of carbon atoms is preferably at least 10, more preferably at least 12, and most preferably at least 15.

The molecular weight of the hydrophobic organic solvent is preferably at least 200, more preferably at least 300, even more preferably at least 500, and most preferably at least 1,000. By thus using a hydrophobic organic solvent having a high molecular weight, together with functioning as a solvent, this compound also carries out a dispersant-like role, minimizing sticking and agglomeration of the particles and making it possible to obtain polymer particles that are stably monodispersed and have a controlled particle size.

High-molecular-weight compounds having recurring units are preferred as the hydrophobic organic solvent with a molecular weight of 200 or more. Examples include hydrocarbon compounds, siloxane compounds and polyalkylene oxide group-containing compounds. These high-molecular-weight compounds are more preferably high-molecular-weight compounds which are water-soluble in a low-molecular-weight state and exhibit hydrophobicity as the molecular weight increases, or hydrophobic organic solvents obtained by polymerizing a monomer having a polar group at the interior of the molecule. By having such polar groups at the interior of the molecule, the subsequently described high-molecular-weight stabilizer readily disperses uniformly within the solvent, further contributing to particle stability. Examples of such polar groups include hydroxyl, ether and carbonyl groups.

Examples of hydrophobic organic solvents that satisfy these conditions include, of the hydrophobic organic solvents mentioned above, polyethers such as polypropylene glycol and polybutylene glycol; and siloxane compounds such as polydimethylsiloxane, polymethylphenylsiloxane, polydiphenylsiloxane and silicone oils.

The viscosity of the hydrophobic organic solvent, although not particularly limited, is preferably at least 1 cP at 25° C.

Illustrative examples of the polymerizable monomer serving as the starting material for the flat elliptical polymer particle of the invention include:
(i) styrene compounds such as styrene, o-methylstyrene, n-methylstyrene, p-methylstyrene, α-methylstyrene, o-ethylstyrene, m-ethylstyrene, p-ethylstyrene, 2,4-dimethylstyrene, p-n-butylstyrene, p-t-butylstyrene, p-n-hexylstyrene, p-n-octylstyrene, p-n-nonylstyrene, p-n-decylstyrene, p-n-dodecylstyrene, p-methoxystyrene, p-phenylstyrene, p-chlorostyrene and 3,4-dichlorostyrene;
(ii) (meth)acrylic esters, including hydrocarbon group-containing (meth)acrylic monomers such as methyl (meth)acrylate, ethyl (meth)acrylate, propyl (meth)acrylate, n-butyl (meth)acrylate, isobutyl (meth)acrylate, pentyl (meth)acrylate, hexyl (meth)acrylate, 2-ethylhexyl (meth)acrylate, octyl (meth)acrylate, nonyl (meth)acrylate, decyl (meth)acrylate, dodecyl (meth)acrylate, lauryl (meth)acrylate, stearyl (meth)acrylate, cyclohexyl (meth)acrylate, isobornyl (meth)acrylate, phenyl (meth)acrylate, toluyl (meth)acrylate and benzyl (meth)acrylate; fluorine-containing (meth)acrylic monomers such as 2,2,2-trifluoroethyl (meth)acrylate, 3,3,3-trifluoropropyl (meth)acrylate, 2-(perfluoroethyl)ethyl (meth)acrylate, 2-perfluoroethyl-2-perfluorobutylethyl (meth)acrylate, 2-perfluoroethyl (meth)acrylate, tetrafluoropropyl (meth)acrylate, perfluoromethyl (meth)acrylate, 1,1,1,3,3,3-hexafluoropropan-2-yl (meth)acrylate, 2-perfluoromethyl-2-perfluoroethylmethyl (meth)acrylate, 2-(perfluorohexyl)ethyl (meth)acrylate, 2-(perfluorodecyl)ethyl (meth)acrylate and 2-(perfluorohexadecyl)ethyl (meth)acrylate; silicon-containing (meth)acrylic monomers such as γ-(methacryloyloxypropyl)trimethoxysilane and γ-(methacryloyloxypropyl)dimethoxymethylsilane; alkoxy group-containing (meth)acrylic monomers such as (poly)ethylene glycol mono(meth)acrylate, 2-methoxyethyl (meth)acrylate and 3-methoxybutyl (meth)acrylate; (poly)alkylene glycol (meth)acrylic monomers such as (poly)propylene glycol mono(meth)acrylate; alkoxy (poly)alkylene glycol (meth)acrylic monomers such as methoxy(poly)ethylene glycol mono(meth)acrylate and methoxy(poly)propylene glycol mono(meth)acrylate; and (meth)acrylic esters containing no reactive functional groups, such as 2-chloroethyl (meth)acrylate and methyl α-chloro(meth)acrylate;
(iii) vinyl carboxylates such as vinyl acetate, vinyl propionate, vinyl benzoate, vinyl butyrate, vinyl formate, vinyl valerate and vinyl pivalate;
(iv) N-vinyl compounds such as N-vinylpyrrole, N-vinylcarbazole, N-vinylindole and N-vinylpyrrolidone;
(v) olefins such as ethylene and propylene;
(vi) fluorinated olefins such as vinyl fluoride, vinylidene fluoride, tetrafluoroethylene and to hexafluoropropylene; and
(vii) conjugated dienes such as butadiene and isoprene.
These may be used singly or two or more may be used in combination.

Of these, the use of styrene compounds, (meth)acrylic acids, (meth)acrylic esters and vinyl esters as the polymerizable monomer is preferred. By using these, it is possible to easily and inexpensively obtain flat elliptical polymer particles having the above-described shape.

Aside from the above polymerizable monomer, an unsaturated monomer having a reactive functional group such as a hydrophilic functional group or an active hydrogen group may be used alone or in combination with the above polymerizable monomer. Examples of such reactive functional groups include amino, carboxyl, hydroxyl, thiol, carbonyl, ether, cyano, amide, alkylene oxide, epoxy and ionic functional groups. One type of functional group may exist by itself, or two or more types may be present together, on the unsaturated monomer. Introducing these reactive functional groups such as hydrophilic functional groups and active hydrogen groups to the interior of the particles or to the surface layer not only enables enhanced functions such as hydrophilicity or oil resistance to be achieved, it also enables their use as auxiliary functional groups that confer various kinds of functionality, such as the formation of a composite structure with inorganic particles or other types of polymer particles, the formation of a crosslinked structure owing to reactions between the functional groups, surface treatment and surface modification due to bonding of the reactive compound, and the imparting of active substances.

Unsaturated monomers having such reactive functional groups are exemplified as shown below. In the explanation that follows, "$C_n$" means "n number of carbon atoms."
(1) Amino Group-Containing Monomers
Examples include amino group-containing (meth)acrylic monomers such as 2-aminoethyl (meth)acrylate, N-propylaminoethyl acrylate, N-ethylaminopropyl (meth)acrylate, N-phenylaminoethyl (meth)acrylate and N-cyclohexylaminoethyl (meth)acrylate; allylamine derivatives such as allylamine and N-methylallylamine; amino group-containing styrene derivatives such as a p-aminostyrene; and triazine derivatives such as 2-vinyl-4,6-diamino-S-triazine. Of these, compounds having a primary or secondary amino group are preferred.

(2) Carboxyl Group-Containing Monomers

Examples include unsaturated carboxylic acids such as (meth)acrylic acid, crotonic acid, cinnamic acid, itaconic acid, maleic acid and fumaric acid; mono($C_{1-8}$ alkyl) esters of itaconic acid such as monobutyl itaconate; mono($C_{1-8}$ alkyl) esters of maleic acid such as monobutyl maleate; vinyl group-containing aromatic carboxylic acids such as vinylbenzoic acid; and salts thereof.

(3) Hydroxyl Group-Containing Monomers

Examples include hydroxyl group-containing (meth)acrylic monomers such as 2-hydroxyethyl (meth)acrylate, 2-hydroxypropyl (meth)acrylate, 3-hydroxypropyl (meth)acrylate and 4-hydroxybutyl (meth)acrylate; hydroxyalkyl vinyl ether monomers such as hydroxyethyl vinyl ether and hydroxybutyl vinyl ether; and hydroxyl group-containing allyl monomers such as allyl alcohol and 2-hydroxyethyl allyl ether.

(4) Thiol (Mercapto) Group-Containing Monomers

Examples include mercapto group-containing (meth)acrylic monomers such as N-(2-mercaptoethyl) acrylamide, N-(2-mercapto-1-carboxyethyl) acrylamide, N-(2-mercaptoethyl) methacrylamide, N-(4-mercaptophenyl) acrylamide, N-(7-mercaptonaphthyl) acrylamide, maleic acid mono (2-mercaptoethylamide), 2-mercaptoethyl (meth)acrylate and 2-mercapto-1-carboxyethyl (meth)acrylate.

(5) Carbonyl Group-Containing Monomers

Examples include vinyl methyl ketone, vinyl hexyl ketone and methyl isopropenyl ketone.

(6) Ether Group-Containing Monomers

Examples include vinyl group-containing ether monomers such as vinyl methyl ether, vinyl ethyl ether and vinyl isobutyl ether.

(7) Cyano Group-Containing Monomers

Examples include acrylonitrile, methacrylonitrile, hexenenitrile, 4-pentenenitrile and p-cyanostyrene.

(8) Amide Group-Containing Monomers

Examples include (meth)acrylamide, α-ethyl (meth)acrylamide, N-methyl (meth)acrylamide, N-butoxymethyl (meth)acrylamide, diacetone (meth)acrylamide, N,N-dimethyl (meth)acrylamide, N,N-diethyl (meth)acrylamide, N,N-dimethyl-p-styrene sulfonamide, N,N-dimethylaminoethyl (meth)acrylamide, N,N-diethylaminoethyl (meth)acrylamide, N,N-dimethylaminopropyl (meth)acrylamide and N,N-diethylaminopropyl (meth)acrylamide.

(9) Epoxy Group-Containing Monomers

Examples include epoxy group-containing (meth)acrylic monomers such as glycidyl (meth)acrylate, (β-methyl)glycidyl (meth)acrylate and 3,4-epoxycyclohexyl (meth)acrylate; epoxy group-containing vinyl monomers such as allyl glycidyl ether and 3,4-epoxyvinylcyclohexane; and di(β-methyl)glycidyl maleate and di(β-methyl)glycidyl fumarate.

(10) Ionic Functional Group-Containing Monomers

The ionic functional groups may be anionic functional groups or cationic functional groups.

Examples of anionic functional groups include carboxyl groups, sulfonic acid groups, phosphoric acid groups, phenolic hydroxyl groups and salts thereof. Examples of cationic functional groups include amino groups, imidazole groups, pyridine groups, amidino groups, and salts thereof.

Anionic functional groups are especially preferred because there are numerous widely used products and plentiful types, and also because the size, shape and other particle characteristics can be efficiently controlled. In addition, of these, because introduction to the interior of the molecule is easy and the stability and safety are excellent, it is preferable for one or more functional group to be selected from among carboxylic groups, sulfonic acid groups, phosphoric acid groups and derivatives thereof.

As for compounds capable of becoming counterions for these ionic functional groups, examples of counterions for anionic functional groups include metal cations, ammonium cations, pyridinium cations and phosphonium cations; examples of counterions for cationic functional groups include halide ions such as the chloride, bromide and iodide ions.

Of the above unsaturated monomers having reactive functional groups, monomers having a hydroxyl group, carboxyl group, amino group, amide group, alkylene oxide group or ionic functional group are preferred; and monomers having a hydroxyl group, carboxyl group, ethylene oxide group or ionic functional group are more preferred. By using these functional groups, the hydrophilicity is stronger and the repulsion between particles obtained in solution is stronger. As a result, the dispersion system has a higher stability and the monodispersibility can be improved even further, enabling a decrease in particle size accuracy due to particle sticking and agglomeration to be mitigated and moreover making it possible to obtain polymer particles of excellent chemical resistance, reactivity, solvent dispersibility, powder dispersibility, and mechanical properties.

During the polymerization reaction, depending on the heat resistant and chemical-resistant applications in which the resulting particles are to be used, a crosslinking agent may be included in a suitable amount of from 0.01 to 80 wt %, based on the total weight of the polymerization ingredients. Illustrative examples of the crosslinking agent include aromatic divinyl compounds such as divinylbenzene, divinylbiphenyl and divinylnaphthalene; (poly)alkylene glycol di(meth)acrylates such as (poly)ethylene glycol di(meth)acrylate, (poly)propylene glycol di(meth)acrylate and (poly)tetramethylene glycol di(meth)acrylate; alkanediol di(meth)acrylates such as 1,6-hexanediol di(meth)acrylate, 1,8-octanediol di(meth)acrylate, 1,9-nonanediol di(meth)acrylate, 1,10-decanediol di(meth)acrylate, 1,12-dodecandiol di(meth)acrylate, 3-methyl-1,5-pentanediol di(meth)acrylate, 2,4-diethyl-1,5-pentanediol di(meth)acrylate, butylethylpropanediol di(meth)acrylate, 3-methyl-1,7-octanediol di(meth)acrylate and 2-methyl-1,8-octanediol di(meth)acrylate; alkanediol di(meth)acrylates such as 1,6-hexanediol di(meth)acrylate, 1,8-octanediol di(meth)acrylate, 1,9-nonanediol di(meth)acrylate, 1,10-decanediol di(meth)acrylate, 1,12-dodecanediol di(meth)acrylate, 3-methyl-1,5-pentanediol di(meth)acrylate, 2,4-diethyl-1,5-pentanediol di(meth)acrylate, butylethylpropanediol di(meth)acrylate, 3-methyl-1,7-octanediol di(meth)acrylate and 2-methyl-1,8-octanediol di(meth)acrylate; polyfunctional (meth)acrylates such as glycerol di(meth)acrylate, pentaerythritol tri(meth)acrylate, pentaerythritol tetra(meth)acrylate, pentaerythritol di(meth)acrylate, glycerol acryloxy di(meth)acrylate, ethoxylated cyclohexane dimethanol di(meth)acrylate, ethoxylated bisphenol A di(meth)acrylate, tricyclodecane dimethanol di(meth)acrylate, propoxylated ethoxylated bisphenol A di(meth)acrylate, 1,1,1-trishydroxymethylethane di(meth)acrylate, 1,1,1-trishydroxymethylethane tri(meth)acrylate, 1,1,1-trishydroxymethylpropane tri(meth)acrylate, caprolactone-modified dipentaerythritol hexa(meth)acrylate, caprolactone-modified hydroxypivalate neopentyl glycol di(meth)acrylate, polyester (meth)acrylate and urethane (meth)acrylate; and compounds such as N,N-divinylaniline, divinyl ether, divinylsulfide and divinylsulfone.

Unsaturated monomers having reactive functional groups such as the above epoxy group-containing (meth)acrylic monomers may also be used as the crosslinking agent.

These crosslinking agents may be used singly or two or more may be used in combination.

Methods for producing crosslinked particles are exemplified by a method that increases the degree of crosslinking by adding the above polyfunctional unsaturated monomer; a method that increases the degree of crosslinking by copolymerizing the above-mentioned reactive group-containing unsaturated monomers under specific pH conditions; and a method (referred to below as "post-crosslinking") in which the above reactive group-containing unsaturated monomers are copolymerized to form particles, after which an organic compound that reacts with the reactive functional groups is placed, in the presence of at least one solvent selected from among water and organic solvents that dissolves the organic compound but does not dissolve the precipitated particles, in a state where the organic compound has impregnated the surface layer alone or both the surface layer and the interior of the particles, thereby inducing crosslinking via reactions of the functional groups on the particles with the reactive group on the organic compound.

In this case, the organic compound for post-crosslinking is exemplified by organic compounds having, for example, a hydroxyl, carboxyl, amino, thiol, carbonyl, ether, cyano, epoxy (glycidyl), amide, isocyanate, carbodiimide, oxazoline or alkylene oxide group as the reactive functional group.

In the production method of the invention, it is especially preferable to use as the unsaturated monomer at least an unsaturated monomer which is hydrophobic and liquid at 25° C.

Preferred examples of such hydrophobic liquid unsaturated monomers include the (i) styrene compounds, (ii) hydrocarbon group-containing (meth)acrylic monomers, fluorine-containing (meth)acrylic monomers and epoxy group-containing (meth)acrylic monomers, (v) olefins, (vi) fluorinated olefins and (vii) conjugated dienes mentioned above as polymerizable monomers; the (9) epoxy group-containing vinyl monomers mentioned above as reactive functional group-containing unsaturated monomers; and the aromatic divinyl compounds, (poly)alkylene glycol di(meth)acrylates, alkanediol di(meth)acrylates and polyfunctional (meth)acrylates mentioned as crosslinking agents.

Also, in the production method of the invention, to efficiently obtain flat elliptical polymer particles, with the use of such a hydrophobic liquid unsaturated monomer, the proportion of hydrophobic liquid ingredients—including the hydrophobic liquid unsaturated monomer and the hydrophobic organic solvent—is set to preferably at least 10 wt %, more preferably at least 20 wt %, even more preferably at least 25 wt %, and most preferably at least 30 wt %, of the total amount of charged ingredients.

In this case, the hydrophobic organic solvent is preferably one having the ability to dissolve the hydrophobic liquid unsaturated monomers but not having the ability to dissolve the flat elliptical polymer particles that form in the polymerization reaction.

Examples of such hydrophobic organic solvents include polyethers such as polypropylene glycol and polybutylene glycol, siloxane compounds such as polydimethylsiloxane, polymethylphenylsiloxane, polydiphenylsiloxane and silicone oils, liquid paraffin, and aliphatic or aromatic hydrocarbons such as heat transfer medium oils.

The viscosity at 25° C. of the charged ingredients as a whole is adjusted to preferably at least 1 cP, more preferably at least 2 cP, even more preferably at least 5 cP, and most preferably at least 10 cP. The upper limit is less than 10,000 cP. At a higher viscosity that this, the yield of flat elliptical polymer particles may decrease.

Adjustment of the viscosity can be easily carried out by means of the viscosities of the organic solvents used or by adding the subsequently described high-molecular-weight stabilizer or the like.

In the production method of the invention, it is preferable to use as the polymerization initiator one type that dissolves in at least one of the water, the hydrophilic organic solvent and the hydrophobic organic solvent, or a combination of two or more types that dissolve in each of the water, the hydrophilic organic solvent and the hydrophobic organic solvent.

In a production method that uses the three types of solvent of the invention, when the three types of solvent have been agitated and mixed and then left to stand, there arises a "fuzzy" state within which co-exist an emulsified layer (bottom layer, or water-rich layer), a dissolved layer (intermediate layer, or hydrophilic solvent-rich layer) and a separated layer (top layer, or hydrophobic solvent-rich layer). Even in the polymerization reaction, the reaction is thought to proceed with the unsaturated monomer dissolved in each of these layers.

In a solvent system that forms this fuzzy state, by additionally using the above-described combination of polymerization initiators, the polymerization reaction on the unsaturated monomer can be made to proceed in a state where at least one of the polymerization initiators used has dissolved in all three solvents—the water, the hydrophilic organic solvent and the hydrophobic organic solvent, that is, in a state where at least one of the polymerization initiators used is present in each of the above emulsified layer, dissolved layer and separated layer. It is presumably on account of this that the shapes of the resulting polymer particles can be more efficiently rendered into flat elliptical shapes.

With regard to the above "combination" of polymerization initiators, when the polymerization initiator is one that dissolves in each of the water, the hydrophilic organic solvent and the hydrophobic organic solvent, a single polymerization initiator may be used by itself. However, in this invention, it is preferable to use in combination at least one water-soluble initiator that dissolves in water and at least one oil-soluble initiator that does not dissolve in water.

In this invention, "water-soluble initiator" refers to an initiator having a solubility in water of at least about 2 g per 100 mL, and "oil-soluble initiator" refers to an initiator having a solubility in water of less than 2 g/100 mL.

In this case, the mixing ratio of the water-soluble initiator and the oil-soluble initiator is not particularly limited, although the weight ratio of water-soluble initiator to oil-soluble initiator is preferably from 99:1 to 1:99, more preferably from 95:5 to 5:95, even more preferably from 90:10 to 10:90, still more preferably from 80:20 to 20:80, and most preferably from 70:30 to 30:70.

Various known polymerization initiators may be used as the polymerization initiators in the invention.

Illustrative examples of water-soluble polymerization initiators include the following water-soluble or ionic polymerization initiators: persulfates such as ammonium persulfate, sodium persulfate and potassium persulfate; and azo-type initiators such as
2,2'-azobis[2-methyl-N-(2-hydroxyethyl)propionamide],
2,2'-azobis(2-amidinopropane) dihydrochloride,
2,2'-azobis(2-methyl-N-phenylpropionamidine) dihydrochloride, 2,2'-azobis[N-(4-chlorophenyl)-2-methylpropionamidine] dihydrochloride,
2,2'-azobis[N-(4-hydroxyphenyl)-2-methylpropionamidine] dihydrochloride,
2,2'-azobis[N-(4-aminophenyl)-2-methylpropionamidine] tetrahydrochloride,
2,2'-azobis[2-methyl-N-(phenylmethyl)propionamidine] dihydrochloride,
2,2'-azobis[2-methyl-N-2-propenylpropionamidine] dihydrochloride,
2,2'-azobis[N-(2-hydroxyethyl)-2-methylpropionamidine] dihydrochloride,
2,2'-azobis[2-(5-methyl-2-imidazolin-2-yl)propane] dihydrochloride,
2,2'-azobis[2-(2-imidazolin-2-yl)propane] dihydrochloride,
2,2'-azobis[2-(4,5,6,7-tetrahydro-1H-1,3-diazepin-2-yl)propane] dihydrochloride,
2,2'-azobis[2-(3,4,5,6-tetrahydropyrimidin-2-yl)propane] dihydrochloride,
2,2'-azobis[2-(5-hydroxy-3,4,5,6-tetrahydropyrimidin-2-yl)propane] dihydrochloride,
2,2'-azobis{2-[1-(2-hydroxyethyl)-2-imidazolin-2-yl] propane} dihydrochloride,
2,2'-azobis-2-cyanopropane-1-sulfonic acid disodium salt, and
sodium 4,4'-azobis(4-cyanopentanoate).

Specific examples of oil-soluble polymerization initiators include peroxides such as benzoyl peroxide, cumene hydroperoxide and t-butyl hydroperoxide; and azo compounds such as azobisisobutyronitrile, azobismethylbutyronitrile, azobisisovaleronitrile, 2,2'-azobis(dimethyl isobutyrate), 2,2'-azobis(N-butyl-2-methylpropionamide), 4,4'-azobis(4-cyanopentanoic acid), 2,2'-azobis(2-amidinopropane) dihydrochloride and 2,2'-azobis(N,N'-dimethylene isobutylamidine) dihydrochloride.

These polymerization initiators may each be used singly or two or more may be used in admixture. It is preferable for the total content of radical polymerization initiator to be generally from 0.01 to 50 parts by weight per 100 parts by weight of the unsaturated monomer.

In the production method of the invention, the pH of the reaction system is not particularly limited, the desired flat elliptical polymer particles generally being obtained without carrying out pH adjustment. However, during the polymerization reaction (at least from a point following the start of heating and up until the time that the reaction is complete), by adjusting the pH of the solution to 0 to 5 or to 9 to 14 and polymerizing the unsaturated monomer, it is possible to obtain monodispersible polymer particles having few agglomerates or impurities while maintaining a flat elliptical shape.

The pH of the reaction solution is preferably from 0 to 4 or from 10 to 14, more preferably from 0 to 3 or from 11 to 14, and most preferably from 0 to 2 or from 12 to 14. When the reaction is made to proceed with the pH shifted to the acidic side, the polymerization reaction proceeds more stably; hence, it is preferable for the pH to be from 0 to 5.

A known pH adjustor may be suitably used to adjust the pH. Examples of pH adjustors include acids such as citric acid, tartaric acid, lactic acid, glycolic acid, hydrochloric acid, nitric acid, sulfuric acid, sodium citrate, sodium lactate, succinic acid, acetic acid, sodium acetate, fumaric acid, malic acid and phosphoric acid; and alkalis such as sodium hydroxide, potassium hydroxide, calcium hydroxide, magnesium hydroxide, sodium carbonate, potassium carbonate, calcium carbonate, ammonium carbonate, ammonia, morpholine, triethanolamine, diethanolamine, dimethylamine, diethylamine, trimethylamine and triethylamine.

Adjustment of the pH may be carried out by, for example, the gradual dropwise addition of a pH adjustor to the reaction solution following the start of the polymerization reaction so as to shift the pH to the acidic or alkaline side.

Alternatively, when the subsequently described persulfate is used as the polymerization initiator, because it breaks down during the polymerization reaction and forms an acid, the pH gradually decreases. In this case, a pH adjustor need not be added.

The pH of the reaction system in this invention is the pH value of the reaction solution in an agitated state, as measured with a pH meter or pH test paper.

The ingredients and composition of the water, hydrophilic organic solvent and hydrophobic organic solvent may be suitably adjusted to impart the features of fine surface irregularities, porosity or large specific surface area to the flat elliptical polymer particles. It is possible in this way to suitably modify the particle surface and interior.

In this invention, by carrying out the above types of adjustments in the solvent composition, it is possible to control the particle size and aspect ratio, the size of fine surface irregularities, and the porosity of the flat elliptical polymer particles, enabling a good balance in performance attributes such as water absorption and oil absorption to be achieved.

The content of unsaturated monomer in the reaction solution is preferably from 1 to 80 wt %, more preferably from 5 to 60 wt %, even more preferably from 10 to 50 wt %, and most preferably from 15 to 45 wt %, of the overall reaction solution. When the unsaturated monomer content exceeds 80 wt %, it is sometimes difficult to efficiently obtain flat elliptical polymer particles in a monodispersed state. On the other hand, when the content is less than 1 wt %, the target flat elliptical polymer particles can be obtained, but the reaction takes a long time to go to completion, which is impractical from an industrial standpoint.

The reaction temperature at the time of polymerization varies also according to the types of solvent and polymerization initiator used, and so cannot be strictly specified, but is typically from about 10° C. to about 200° C., preferably from 30 to 130° C., and more preferably from 40 to 90° C.

The reaction time is not particularly limited, so long as it is the time needed for the intended reaction to go substantially to completion, and is governed largely by such factors as the type, content and concentration of the unsaturated monomer, the viscosity of the solution, and the intended particle size. For example, within the above-indicated temperature range, the reaction time is typically from 1 to 72 hours, and preferably from about 2 hours to about 24 hours.

During production of the polymer particles used in this invention, depending on the polymerization method, (polymer) dispersants, stabilizers, emulsifying agents (surfactants) and the like may also be included in a suitable amount of from 0.01 to 50 wt %, based on the starting monomer mentioned above.

Dispersants and stabilizers are exemplified by various types of hydrophobic or hydrophilic dispersants and stabilizers, including polystyrene derivatives such as polyhydroxystyrene, polystyrenesulfonic acid, hydroxystyrene-(meth)acrylic ester copolymers, styrene-(meth)acrylic ester copolymers and styrene-hydroxystyrene-(meth)acrylic ester copolymers; poly(meth)acrylic acid derivatives such as poly (meth)acrylic acid, poly(meth)acrylamide, polyacrylonitrile, polyethyl (meth)acrylate and polybutyl (meth)acrylate; polyethers such as polyethylene glycol, poly(methyl vinyl ether), poly(ethyl vinyl ether), poly(butyl vinyl ether) and poly(isobutyl vinyl ether), and derivatives thereof; cellulose and cellulose derivatives such as methyl cellulose, cellulose acetate, cellulose nitrate, hydroxymethyl cellulose, hydroxyethyl cellulose, hydroxypropyl cellulose and carboxymethyl cellulose; polyvinyl acetate derivatives such as polyvinyl alcohol, polyvinyl butyral, polyvinyl formal and polyvinyl acetate; nitrogen-containing polymer derivatives such as polyvinyl pyridine, polyvinyl pyrrolidone, polyethyleneimine and poly-2-methyl-2-oxazoline; and polyvinyl halide derivatives such as polyvinyl chloride and polyvinylidene chloride. These may be of one type used alone or two or more may be used in combination.

The emulsifying agents (surfactants) are exemplified by anionic emulsifying agents, including alkyl sulfates such as sodium dodecyl sulfate, alkylbenzenesulfonates such as sodium dodecylbenzenesulfonate, alkylnaphthalenesulfonates, fatty acid salts, alkyl phosphates and alkyl sulfosuccinates; cationic emulsifying agents such as alkylamine salts, quaternary ammonium salts, alkyl betaines and amine oxides; and nonionic emulsifying agents such as polyoxyethylene alkyl ethers, polyoxyethylene alkyl allyl ethers, polyoxyethylene alkyl phenyl ethers, sorbitan fatty acid esters, glycerol fatty acid esters, sucrose fatty acid esters and polyoxyethylene fatty acid esters. These may be used singly or two or more may be used in combination.

By using these dispersants, stabilizers, emulsifying agents and the like, the length, breadth, thickness and other properties of the flat elliptical polymer particles can be more stably controlled.

Depending on such considerations as the intended use of the resulting particles, a catalyst (reaction accelerator) may be included at the time of the polymerization reaction. The content thereof may be set to a suitable amount that does not adversely affect the particle properties, such as from 0.01 to 20 wt % of the total weight of the unsaturated monomer.

The catalyst is not particularly limited so long as it is a positive catalyst, and may be suitably selected from among known catalysts and used. Examples include tertiary amines such as benzyldimethylamine, triethylamine, tributylamine, pyridine and triphenylamine; quaternary ammonium compounds such as triethylbenzylammonium chloride and tetramethylammonium chloride; phosphines such as triphenylphosphine and tricyclophosphine; phosphonium compounds such as benzyl trimethylphosphonium chloride; imidazole compounds such as 2-methylimidazole and 2-methyl-4-ethylimidazole; alkali metal hydroxides such as potassium hydroxide, sodium hydroxide and lithium hydroxide; alkali metal carbonates such as sodium carbonate and lithium carbonate; alkali metal salts of organic acids; and halides that exhibit Lewis acid properties, such as boron trichloride, boron trifluoride, tin tetrachloride and titanium tetrachloride, or complex salts thereof. These may be used singly or two or more may be used in combination.

At the time of the polymerization reaction, in order to adjust the size, shape, quality and the like of the resulting flat elliptical polymer particles, it is also possible to add a compound that is soluble in water or another polar solvent and undergoes electrolytic dissociation into cations and anions, such that the solution exhibits electrical conductivity.

Examples include salts, inorganic acids, inorganic bases, organic acids, organic bases and ionic liquids. The content thereof is a suitable amount that does not adversely affect the particle properties, and may be set to, for example, from 0.01 to 80 wt % of the total weight of the polymerization ingredients.

[Uses of Flat Elliptical Polymer Particles]

The flat elliptical polymer particles of the invention can be used in polymer molded or formed articles such as plastics, containers, paints, paint films, fibers and building materials. Also, because they are effective as well in terms of UV scattering properties, they can be used for the protection of UV-sensitive contents, such as in filters, packaging materials, containers, paints, paint films, inks, fibers, building materials, recording media, image displaying devices and solar cell covers, and can also check the decomposition of compounds unstable to light.

In addition, compared with conventional spherical particles, the flat elliptical polymer particles of the invention can increase the strength of molded or formed articles. Hence, because the strength of molded or formed articles can be maintained even with high loadings of particles, use in light-diffusing plates and light-diffusing sheets that utilize optical characteristics is also possible.

The flat elliptical polymer particles of the invention may be dispersed in water, a hydrophilic organic solvent, a hydrophobic organic solvent or a mixed solvent thereof and used as a dispersion. The hydrophilic organic solvent and hydrophobic organic solvent are exemplified by the same solvents mentioned above in connection with the polymer particle production method.

The flat elliptical polymer particles of the invention may be used as an additive in liquids and formed articles such as paint films, film, sheet stock and paper.

The flat elliptical polymer particle-containing composition of the invention may be widely used in, for example, light scattering agents and optical filter materials, colorants, cosmetics, absorbents, adsorbents, inks, adhesives, electromagnetic shielding materials, fluorescence sensors, biological markers, recording media, recording elements, polarizing materials, drug supports for drug delivery systems (DDS), biosensors, DNA chips and diagnostic agents.

Also, by incorporating the flat elliptical polymer particles of the invention into a precursor, and carrying out firing treatment such as curing, carbonization or sintering, a thermally cavitated product having pores corresponding to the particle shapes can be produced.

In addition, because the hardness of the inventive particles can be increased by raising the degree of crosslinking, these particles can even be used in the production of molded or formed products that require the application of a level of pressure at which, in conventional polymers, maintaining the pore shapes is difficult.

Using window glass products or interior decoration products such as curtains and wall materials to block light or ultraviolet radiation from entering into a room, car or the like is useful not only for preventing sunburn and other adverse effects to the human body, but also for preventing the deterioration of decorative objects within the room or car.

The flat elliptical polymer particles of the invention are also suitable as additives for cosmetics. Expansion into thermoforming applications and applications that use a large amount of organic solvent where addition has hitherto been difficult is now possible while retaining such desirable features of the flat elliptical polymer particles as their low weight and their light scattering properties, tactile qualities, flowability and solution dispersibility. The flat elliptical polymer particles of the invention, owing to their distinctive shapes, have an adhesive strength differing from that of ordinary spherical particles, and are thus effective for improving both the bonding strength of pressed compacts of cosmetic foundation and also the holding power following application. In addition, the optical characteristics make the skin appear lighter and can enhance the covering power due to a shading effect. Also, due to the slip properties particular to the particle shape, spreadability over the skin is excellent and furrows in the skin texture are finely filled, making wrinkles and pores inconspicuous, and the flowability of the overall product can be freely controlled. Also, the adhesive strength and holding power can be utilized to increase the amount of polymer addition in the overall product, enabling the discovery of entirely new cosmetic effects. The amount of addition, based on the overall product content, is preferably from 0.1 to 50 wt %, and more preferably from 0.5 to 30 wt %. This amount may be suitably adjusted according to the intended use and purpose, such as enhancing the light scattering properties (e.g., the UV scattering effect and the shading effect), flowability, moldability and adhesion, and the finished look. According to investigations by the inventors, as an additive for cosmetics, the addition of 1 to 20 wt % is especially preferred. Suitable adjustment and use in combination with commercially available particles is also possible.

In particular, examples of cosmetics in which the advantageous effects are high include skin care products, hair products, antiperspirants, make-up products, UV protection products and scented products. Specific examples include base cosmetics such as milky emulsions, creams, lotions, calamine lotion, sunscreens, makeup base, suntan lotions, aftershave lotions, preshave lotions, packs, cleansing materials, facial cleansers, cosmetics for acne, and essences; makeup cosmetics such as foundation, face powder, mascara, eye shadow, eyeliner, eyebrow, cheek, nail color, lip cream and lipstick; and also shampoos, rinses, conditioners, hair colors, hair tonics, setting agents, body powders, hair growth promoters, deodorants, depilatories, soaps, body shampoos, bath preparations, hand soaps and perfumes.

The form of the product is not particularly limited. Use is possible in various forms, such as liquids, emulsions, creams, solids, pastes, gels, powders, multi-layer preparations, mousses and sprays. Useful effects can be expected of the crosslinked polymer particles as an additive in these cosmetics.

The flat elliptical polymer particles of the invention can be utilized as additives for printing inks that may be used in, for example, screen printing, offset printing, process printing, gravure printing, pad printing, coaters and inkjet printing; as additives for writing implement inks in marking pens, ballpoint pens, fountain pens, calligraphy pens and magic markers; and as additives for writing materials such as crayons, artist's paints and erasers.

The flat elliptical polymer particles of the invention are suitable as additives for paints that may be used in brush painting, spray painting, electrostatic spray painting, electrodeposition painting, flow coating, roller coating and dip coating. For example, they are suitable as additives for paints and coatings that may be used on transportation equipment such as automobiles, railway cars, helicopters, ships, bicycles, snowmobiles, ropeways, lifts, hovercrafts and motorcycles; building members such as window sashes, shutters, cisterns, doors, balconies, outside panels for construction, roofing, staircases, skylights and concrete walls; the exterior walls and interior finish on the inside and outside of buildings; roadway members such as guardrails, pedestrian bridges, sound insulating walls, road signs, highway sidewalls, elevated railway bridges, and bridges; industrial plant members such as tanks, pipes, towers and smokestacks; agricultural facilities such as PVC and other types of greenhouses, silos and agricultural sheeting; telecommunications facilities such as utility poles, transmission towers and parabolic antennas; electrical equipment such as electrical service boxes, lighting equipment, outdoor air conditioners, washing machines, refrigerators and electric ranges, as well as covers for these; and other articles such as monuments, gravestones, paving materials, windscreens, waterproof sheeting and curing sheets for construction.

The form of the paint is exemplified by not only solvent-based paints, but also water-dispersed paints, non-water-dispersed paints, powder paints and electrodeposition paints, and may be suitably selected as needed.

EXAMPLES

Working Examples and Comparative Examples are given below by way of illustration, although the invention is not limited to these Examples. Evaluations in the Working Examples and Comparative Examples were carried out by the following methods.

(1) Sphere-Equivalent Volume Mean Particle Size (MV) of Polymer Particles

The volume mean particle size was measured using the MICROTRACK MT3000 (Nikkiso Co., Ltd.).

(2) Aspect Ratio of Polymer Particles

A scanning electron microscope (S-4800, from Hitachi High Technologies Corporation; referred to below as "SEM") was used to capture photographs at a magnification at which particle measurement is possible (300 to 30,000×), thereby rendering the flat elliptical polymer particles obtained into two-dimensional images. In the images, 100 particles were randomly sampled and the length (L) of the flat region, breadth (D) of the flat region and thickness (T) for each particle were measured. Based on these measurements, the following were determined:

average value $P1_{AV}$ of the aspect ratio L/D;
average value $P2_{AV}$ of the aspect ratio D/T; and
average value $P3_{AV}$ of the aspect ratio L/T.

The average length $L_{AV}$, average breadth $D_{AV}$ and average thickness $T_{AV}$ of the particles were similarly calculated after measuring the length L, breadth D and thickness T of 100 randomly sampled particles.

(3) Specific Surface Area (SB)

The specific surface area (SB) was measured by the nitrogen gas adsorption method using an automatic specific area/pore size distribution measuring instrument (BELSORP-max, from Bel Japan, Inc.).

(4) Theoretical Specific Surface Area (SD)

Letting 2r (m) be the volume mean particle size, r (m) be the radius and G (g/m$^3$) be the density of a polymer particle, the surface area S' (m$^2$) and volume V (m$^3$) of a spherical particle of radius r (m) are expressed as follows.

Surface area of spherical particle of radius $r$ (m): $S'$ (m$^2$)=$4\pi r^2$

Volume of spherical particle of radius $r$ (m): $V$ (m$^3$) =$4\pi r^3/3$

In this case, the number N of particles contained in one gram of particles is expressed as follows.

Number of particles contained in one gram of particles: $N=1/VG$

Therefore, the theoretical specific surface area SD (m$^2$/g) of spherical particles calculated from the polymer particles is expressed as follows.

$SD$ (m$^2$/g)=$S'N=S'/VG=3/rG$ (5) Bulk Density of Polymer Particles

Calculated as the loose bulk density using Method 1 ("Measurement in a graduated cylinder") of the test methods specified in the Japanese, European and U.S. Pharmacopoeias. Units are in g/mL.

(6) Measurement of Water Absorption

A dried polymer particle powder was dispersed in water to a concentration of about 2 wt % and left at rest for one day, following which it was re-dispersed and then filtered under reduced pressure using a glass filter. The glass filter used in filtration was then subjected to 30 minutes of centrifugation at 3,000 rpm using a centrifuge (CR-20GII, from Hitachi High Technologies Corporation), following which the resulting polymer particle powder was dried. The weight of the powder before and after drying was measured, and the difference in weight was treated as the water absorption.

(7) Measurement of Oil Absorption

Oil absorption was measured in accordance with the boiled linseed oil method described in JIS K 5101.

(8) pH Measurement

The pH of the reaction mixture in an agitated state was determined by visually judging the change in color using pH test paper (from Whatman).

[1] Production of Polymer Particles and Evaluation of Their Properties

Working Example 1-1

The ingredients shown below were charged all at once into a 2,000 mL flask and stirred at room temperature (here and below, 25° C.) for one hour. At this time, the liquid phase was in a state where an aqueous phase portion, an emulsified phase portion and an oil phase portion are intermingled. The pH of the system was measured and found to be 7.

Next, the solution was set to an oil bath temperature of 75° C. and, under a stream of nitrogen, heating and stirring (200 rpm) were begun. The polymerization reaction was carried out for 8 hours, giving a polymethyl methacrylate particle dispersion. The pH of the reaction system before the start of heating was 7, the pH of the reaction system two hours after the start of heating was 2, and the pH of the reaction system at the time of reaction completion was 1.

| Water | 950.0 g |
| Methanol | 45.0 g |
| Polypropylene glycol (#3000) | 100.0 g |
| Polyvinyl pyrrolidone (K-15) | 42.5 g |
| Sorbitan monooleate | 12.0 g |
| Azobisisobutyronitrile (AIBN) (oil-soluble) | 4.5 g |
| Ammonium persulfate (water-soluble) | 9.5 g |
| Methyl methacrylate | 600.0 g |

The resulting particle dispersion was transferred to a separate 3,000 mL flask and the synthesis vessel (the flask and the stirring element) was checked for deposits; a clean state was observed with substantially no agglomerate.

Next, using a known suction filtration apparatus, the particle dispersion was filtered and the resulting filtered matter was repeatedly (5 times) washed with methanol and filtered, and then vacuum dried, giving Polymer Particle A1.

One hundred of the resulting particles were randomly sampled and their shapes examined with the SEM. As shown in FIGS. 1 and 2, the particles were flat elliptical polymer particles having fine particles with a mean particle size of 5.0 μm attached to the surface layer portion and surface thereof.

The flat regions of the particles had an average length ($L_{AV}$) of 91 μm and an average breadth ($D_{AV}$) of 44 μm. The average thickness ($T_{AV}$) of the particles was 10 μm. The particles were checked for extraneous matter, but substantially no deformed matter such as agglomerates or mutually sticking particles was observed.

Working Example 1-2

The ingredients shown below were charged all at once into a 2,000 mL flask and stirred at room temperature for one hour. At this time, the liquid phase was in a state where an aqueous phase portion, an emulsified phase portion and an oil phase portion are intermingled. The pH of the system was measured and found to be 7.

Next, the solution was set to an oil bath temperature of 75° C. and, under a stream of nitrogen, heating and stirring (300 rpm) were begun. The polymerization reaction was carried out for 8 hours, giving a polymethyl methacrylate particle dispersion. The pH of the reaction system before the start of heating was 7, the pH of the reaction system two hours after the start of heating was 2, and the pH of the reaction system at the time of reaction completion was 1.

| Water | 760.0 g |
| Ethanol | 22.5 g |
| Polypropylene glycol (#3000) | 80.0 g |
| Polyvinyl pyrrolidone (K-15) | 45.0 g |
| Sucrose ester of lauric acid | 4.0 g |
| Azobisisobutyronitrile (AIBN) (oil-soluble) | 2.4 g |
| Ammonium persulfate (water-soluble) | 2.4 g |
| Methyl methacrylate | 480.0 g |

The resulting particle dispersion was transferred to a separate 3,000 mL flask and the synthesis vessel (the flask and the stirring element) was checked for deposits; a clean state was observed with substantially no agglomerate.

Next, using a known suction filtration apparatus, the particle dispersion was filtered and the resulting filtered matter was repeatedly (5 times) washed with methanol and filtered, and then vacuum dried, giving Polymer Particle A2.

One hundred of the resulting particles were randomly sampled and their shapes examined with the SEM. The particles were flat elliptical polymer particles having fine particles with a mean particle size of 2.2 μm attached to the surface layer portion and surface thereof.

The flat regions of the particles had an average length ($L_{AV}$) of 42 μm and an average breadth ($D_{AV}$) of 8 μm. The average thickness ($T_{AV}$) of the particles was 4 μm. The particles were checked for extraneous matter, but substantially no deformed matter such as agglomerates or mutually sticking particles was observed.

Working Example 1-3

The ingredients shown below were charged all at once into a 2,000 mL flask and stirred at room temperature for one hour. At this time, the liquid phase was in a state where an aqueous phase portion, an emulsified phase portion and an oil phase portion are intermingled. The pH of the system was measured and found to be 7.

Next, the solution was set to an oil bath temperature of 85° C. and, under a stream of nitrogen, heating and stirring (400 rpm) were begun. The polymerization reaction was carried out for 8 hours, giving a polymethyl methacrylate particle dispersion. The pH of the reaction system before the start of heating was 7, the pH of the reaction system two hours after the start of heating was 2, and the pH of the reaction system at the time of reaction completion was 1.

| | |
|---|---:|
| Water | 1,120.0 g |
| Methanol | 22.5 g |
| Polypropylene glycol (#3000) | 80.0 g |
| Polyvinyl pyrrolidone (K-15) | 45.0 g |
| Polyethylene oxide (Mw, 300,000) | 4.0 g |
| Benzoyl peroxide (oil-soluble) | 1.5 g |
| Sodium persulfate (water-soluble) | 3.5 g |
| Methyl methacrylate | 480.0 g |

The resulting particle dispersion was transferred to a separate 3,000 mL flask and the synthesis vessel (the flask and the stirring element) was checked for deposits; a clean state was observed with substantially no agglomerate.

Next, using a known suction filtration apparatus, the particle dispersion was filtered and the resulting filtered matter was repeatedly (5 times) washed with methanol and filtered, and then vacuum dried, giving Polymer Particle A3.

One hundred of the resulting particles were randomly sampled and their shapes examined with the SEM. The particles were flat elliptical polymer particles having fine particles with a mean particle size of 0.3 μm attached to the surface layer portion and surface thereof.

The flat regions of the particles had an average length ($L_{AV}$) of 9 μm and an average breadth ($D_{AV}$) of 3 μm. The average thickness ($T_{AV}$) of the particles was 1 μm. The particles were checked for extraneous matter, but substantially no deformed matter such as agglomerates or mutually sticking particles was observed.

Working Example 1-4

The ingredients shown below were charged all at once into a 2,000 mL flask and stirred at room temperature for one hour. At this time, the liquid phase was in a state where an aqueous phase portion, an emulsified phase portion and an oil phase portion are intermingled. The pH of the system was measured and found to be 7.

Next, the solution was set to an oil bath temperature of 80° C. and, under a stream of nitrogen, heating and stirring (300 rpm) were begun. The polymerization reaction was carried out for 8 hours, giving a styrene-2-hydroxyethyl methacrylate copolymer particle dispersion. The pH of the reaction system before the start of heating was 7, the pH of the reaction system two hours after the start of heating was 3, and the pH of the reaction system at the time of reaction completion was 1.

| | |
|---|---:|
| Water | 864.0 g |
| Methanol | 416.0 g |
| Polypropylene glycol (#2000) | 65.0 g |
| Polyvinyl pyrrolidone (K-30) | 15.0 g |
| Polyethylene oxide (Mw, 100,000) | 6.5 g |
| Dimethyl 2,2'-azobis(isobutyrate) (oil-soluble) | 2.1 g |
| Ammonium persulfate (water-soluble) | 1.8 g |
| Styrene | 357.0 g |
| 2-Hydroxyethyl methacrylate | 63.0 g |

The resulting particle dispersion was transferred to a separate 3,000 mL flask and the synthesis vessel (the flask and the stirring element) was checked for deposits; a clean state was observed with substantially no agglomerate.

Next, using a known suction filtration apparatus, the particle dispersion was filtered and the resulting filtered matter was repeatedly (5 times) washed with a mixture of methanol and water (weight ratio=7:3) and filtered, and then vacuum dried, giving Polymer Particle A4. A portion of the resulting particles was measured with a Fourier transform infrared spectrophotometer (here and below, FT-IR8200PC, from Shimadzu Corporation). An absorption peak at a wave number of 700 (cm$^{-1}$) attributable to the benzene ring of styrene, and an absorption peak at a wave number of 3,000 (cm$^{-1}$) attributable to hydroxyl groups were obtained, confirming that this was the copolymer.

One hundred of the resulting particles were randomly sampled and their shapes examined with the SEM. The particles were flat elliptical polymer particles having fine particles with a mean particle size of 4.6 μm attached to the surface layer portion and surface thereof.

The flat regions of the particles had an average length ($L_{AV}$) of 148 μm and an average breadth ($D_{AV}$) of 12 μm. The average thickness ($T_{AV}$) of the particles was 6 μm. The particles were checked for extraneous matter, but substantially no deformed matter such as agglomerates or mutually sticking particles was observed.

Working Example 1-5

The ingredients shown below were charged all at once into a 2,000 mL flask and stirred at room temperature for one hour. At this time, the liquid phase was in a state where an aqueous phase portion, an emulsified phase portion and an oil phase portion are intermingled. The pH of the system was measured and found to be 7.

Next, the solution was set to an oil bath temperature of 75° C. and, under a stream of nitrogen, heating and stirring (250 rpm) were begun. The polymerization reaction was carried out for 8 hours, giving a methyl methacrylate-ethylene glycol dimethacrylate copolymer particle dispersion. The pH of the reaction system before the start of heating was 7, the pH of the reaction system two hours after the start of heating was 2, and the pH of the reaction system at the time of reaction completion was 1.

| | |
|---|---:|
| Water | 912.0 g |
| Ethanol | 27.0 g |
| Polypropylene glycol (#3000) | 96.0 g |
| Polyvinyl pyrrolidone (K-15) | 48.0 g |
| Sucrose ester of lauric acid | 9.6 g |
| Azobisisobutyronitrile (AIBN) (oil-soluble) | 2.8 g |
| Ammonium persulfate (water-soluble) | 3.2 g |
| Methyl methacrylate | 580.0 g |
| Ethylene glycol dimethacrylate | 5.8 g |

The resulting particle dispersion was transferred to a separate 3,000 mL flask and the synthesis vessel (the flask and the stirring element) was checked for deposits; a clean state was observed with substantially no agglomerate.

Next, using a known suction filtration apparatus, the particle dispersion was filtered and the resulting filtered matter was repeatedly (5 times) washed with methanol and filtered, and then vacuum dried, giving Polymer Particle A5.

One hundred of the resulting particles were randomly sampled and their shapes examined with the SEM. As shown in FIG. 3, the particles were flat elliptical polymer particles having fine particles with a mean particle size of 1.2 μm attached to the surface layer portion and surface thereof.

The flat regions of the particles had an average length ($L_{AV}$) of 35 μm and an average breadth ($D_{AV}$) of 8 μm. The average thickness ($T_{AV}$) of the particles was 2 μm. The particles were checked for extraneous matter, but substantially no deformed matter such as agglomerates or mutually sticking particles was observed.

Working Example 1-6

The ingredients shown below were charged all at once into a 2,000 mL flask and stirred at room temperature for one hour. At this time, the liquid phase was in a state where an aqueous phase portion, an emulsified phase portion and an oil phase portion are intermingled. The pH of the system was measured and found to be 7.

Next, the solution was set to an oil bath temperature of 75° C. and, under a stream of nitrogen, heating and stirring (400 rpm) were begun. The polymerization reaction was carried out for 8 hours, giving a methyl methacrylate-ethylene glycol dimethacrylate copolymer particle dispersion. The pH of the reaction system before the start of heating was 7, the pH of the reaction system two hours after the start of heating was 2, and the pH of the reaction system at the time of reaction completion was 1.

| | |
|---|---|
| Water | 912.0 g |
| Ethanol | 62.2 g |
| Polypropylene glycol (#3000) | 68.0 g |
| Polyvinyl pyrrolidone (K-15) | 58.0 g |
| Sucrose ester of lauric acid | 12.0 g |
| Dimethyl 2,2'-azobis(isobutyrate) (oil-soluble) | 1.8 g |
| Ammonium persulfate (water-soluble) | 4.2 g |
| Methyl methacrylate | 555.0 g |
| Ethylene glycol dimethacrylate | 5.6 g |

The resulting particle dispersion was transferred to a separate 3,000 mL flask and the synthesis vessel (the flask and the stirring element) was checked for deposits; a clean state was observed with substantially no agglomerate.

Next, using a known suction filtration apparatus, the particle dispersion was filtered and the resulting filtered matter was repeatedly (5 times) washed with methanol and filtered, and then vacuum dried, giving Polymer Particle A6.

One hundred of the resulting particles were randomly sampled and their shapes examined with the SEM. As shown in FIG. 3, the particles were flat elliptical polymer particles having fine particles with a mean particle size of 0.8 μm attached to the surface layer portion and surface thereof.

The flat regions of the particles had an average length ($L_{AV}$) of 58 μm and an average breadth ($D_{AV}$) of 4 μm. The average thickness ($T_{AV}$) of the particles was 2 μm. The particles were checked for extraneous matter, but substantially no deformed matter such as agglomerates or mutually sticking particles was observed.

Working Example 1-7

The ingredients shown below were charged all at once into a 2,000 mL flask and stirred at room temperature for one hour. At this time, the liquid phase was in a state where an aqueous phase portion, an emulsified phase portion and an oil phase portion are intermingled. The pH of the system was measured and found to be 7.

Next, the solution was set to an oil bath temperature of 80° C. and, under a stream of nitrogen, heating and stirring (400 rpm) were begun. The polymerization reaction was carried out for 8 hours, giving a methyl methacrylate-glycidyl methacrylate copolymer particle dispersion. The pH of the reaction system before the start of heating was 7, the pH of the reaction system two hours after the start of heating was 2, and the pH of the reaction system at the time of reaction completion was 1.

| | |
|---|---|
| Water | 1,116.0 g |
| Methanol | 124.0 g |
| Polypropylene glycol (#3000) | 85.0 g |
| Polyvinyl pyrrolidone (K-15) | 7.5 g |
| Sorbitan monooleate | 12.5 g |
| Azobisisobutyronitrile (AIBN) (oil-soluble) | 4.6 g |
| Ammonium persulfate (water-soluble) | 6.9 g |
| Methyl methacrylate | 368.0 g |
| Glycidyl methacrylate | 92.0 g |

The resulting particle dispersion was transferred to a separate 3,000 mL flask and the synthesis vessel (the flask and the stirring element) was checked for deposits; a clean state was observed with substantially no agglomerate.

Next, using a known suction filtration apparatus, the particle dispersion was filtered and the resulting filtered matter was repeatedly (5 times) washed with methanol and filtered, and then vacuum dried, giving Polymer Particle A7.

One hundred of the resulting particles were randomly sampled and their shapes examined with the SEM. The particles were flat elliptical polymer particles having fine particles with a mean particle size of 4.6 μm attached to the surface layer portion and surface thereof.

The flat regions of the particles had an average length ($L_{AV}$) of 83 μm and an average breadth ($D_{AV}$) of 22 μm. The average thickness ($T_{AV}$) of the particles was 4 μm. The particles were checked for extraneous matter, but substantially no deformed matter such as agglomerates or mutually sticking particles was observed.

A portion of the resulting particles was measured with a Fourier transform infrared spectrophotometer. The peak at a wave number of 910 (cm$^-$) attributable to epoxy groups was confirmed to be smaller than before synthesis.

Comparative Example 1-1

In Working Example 1-1, aside from not using azobisisobutyronitrile and changing the amount of ammonium persulfate used to 14.0 g, a polymethyl methacrylate particle dispersion was obtained in the same way as in Working Example 1-1. The pH of the reaction system before the start of heating was 7, the pH of the reaction system two hours after the start of heating was 2, and the pH of the reaction system at the time of reaction completion was 1.

The resulting particle dispersion was transferred to a separate 3,000 mL flask and the synthesis vessel (the flask and the stirring element) was checked for deposits; a clean state was observed with substantially no agglomerate.

Next, using a known suction filtration apparatus, the particle dispersion was filtered and the resulting filtered matter was repeatedly (5 times) washed with methanol and filtered, and then vacuum dried, giving Polymer Particle B1.

One hundred of the resulting particles were randomly sampled and their shapes examined with the SEM. As shown in FIGS. 3 and 4, the particles were elliptical polymer particles without a flat region. The particles had an average length ($L_{AV}$) of 28 μm and an average aspect ratio ($P_{AV}$) of 4.3. The particles were checked for extraneous matter, but substantially no deformed matter such as agglomerates or mutually sticking particles was observed.

Comparative Example 1-2

In Working Example 1-1, aside from not using ammonium persulfate and changing the amount of azobisisobutyronitrile used to 14.0 g, a polymethyl methacrylate particle dispersion was obtained in the same way as in Working Example 1-1. The pH of the reaction system before the start of heating was 7, and the pH of the reaction system two hours after the start of heating was also 7.

The resulting particle dispersion was transferred to a separate 3,000 mL flask and the synthesis vessel (the flask and the stirring element) was checked for deposits; masses of agglomerate from precipitated polymer were observed on the inner periphery of flask and on the stirring element.

Next, using a known suction filtration apparatus, the particle dispersion was filtered and the resulting filtered matter was repeatedly (5 times) washed with methanol and filtered, and then vacuum dried, giving Polymer Particle B2.

One hundred of the resulting particles were randomly sampled and their shapes examined with the SEM, whereupon the particles were found to be elliptical polymer particles without a flat region. The particles had an average length ($L_{AV}$) of 52 μm and an average aspect ratio ($P_{AV}$) of 3.7.

Comparative Example 1-3

A suspension was prepared by charging the compounds shown below all at once into a 2,000 mL flask, and stirring at 1,000 rpm with a dispersion mixer stirring element. The suspension was set to an oil bath temperature of 80° C. and heated and stirred for 8 hours under a stream of nitrogen, giving a particle dispersion. Next, centrifugal separation was repeated five times, and classifying and washing operations were carried out, thereby giving spherical polymer particles B3 of polymethyl methacrylate alone having an average particle size of 5 μm.

| Water | 1,386.5 g |
|---|---|
| Methyl methacrylate | 173.4 g |
| Lauryl peroxide | 8.6 g |
| Polyvinyl pyrrolidone (K-30) | 17.3 g |

Comparative Example 1-4

Aside from cutting in half the amount of polyvinyl pyrrolidone (K-30) used, spherical polymer particles B4 of polymethyl methacrylate alone having an average particle size of 100 μm were produced in the same way as in Comparative Example 1-3.

Table 1 below shows the shape, particle ingredients, volume mean particle size (MV), average length of the flat region ($L_{AV}$), average breadth of the flat region ($D_{AV}$), average thickness ($T_{AV}$), average value $P1_{AV}$ of the aspect ratio L/D, average value $P2_{AV}$ of the aspect ratio D/T and average value $P3_{AV}$ of the aspect ratio L/T for the polymer particles obtained in each of the above Working Examples and Comparative Examples.

TABLE 1

|  |  | Polymer particle | Ingredients | Main shape | MV (μm) | $L_{AV}$ (μm) | $D_{AV}$ (μm) | $T_{AV}$ (μm) | $P1_{AV}$ | $P2_{AV}$ | $P3_{AV}$ |
|---|---|---|---|---|---|---|---|---|---|---|---|
| Working Example | 1-1 | A1 | methyl methacrylate | flat elliptical | 38 | 91 | 44 | 10 | 2.1 | 4.4 | 9.1 |
|  | 1-2 | A2 | methyl methacrylate | flat elliptical | 25 | 42 | 8 | 4 | 5.3 | 2 | 10.5 |
|  | 1-3 | A3 | methyl methacrylate | flat elliptical | 6 | 9 | 3 | 1 | 3 | 3 | 9 |
|  | 1-4 | A4 | styrene 2-hydroxyethyl methacrylate | flat elliptical | 41 | 148 | 12 | 6 | 12.3 | 2 | 24.7 |
|  | 1-5 | A5 | methyl methacrylate ethylene glycol dimethacrylate | flat elliptical | 14 | 35 | 8 | 2 | 4.4 | 4 | 17.5 |
|  | 1-6 | A6 | methyl methacrylate ethylene glycol dimethacrylate | flat elliptical | 23 | 58 | 4 | 2 | 14.5 | 2 | 29 |
|  | 1-7 | A7 | methyl methacrylate glycidyl methacrylate | flat elliptical | 36 | 83 | 22 | 4 | 3.8 | 5.5 | 20.8 |
| Comparative Example | 1-1 | B1 | methyl methacrylate | elliptical/needle-shaped | 13 | 28 | 7 | 7 | 4.3 | 1 | 4.3 |
|  | 1-2 | B2 | methyl methacrylate | elliptical/needle-shaped | 30 | 52 | 14 | 14 | 3.7 | 1 | 3.7 |
|  | 1-3 | B3 | methyl methacrylate | spherical | 5 | 5 | 5 | 5 | 1 | 1 | 1 |
|  | 1-4 | B4 | methyl methacrylate | spherical | 100 | 100 | 100 | 100 | 1 | 1 | 1 |

Table 2 below shows the specific surface area (SB), theoretical specific surface area (SD), and ratio (SB/SD) therebetween, and also the bulk density, water absorption and oil absorption, for the polymer particles obtained in the above Working Examples and Comparative Examples.

TABLE 2

|  |  | Polymer particle | Main shape | SB (m²/g) | SD (m²/g) | SB/SD | Bulk density (g/mL) | Water absorption (g/100 g) | Oil absorption (g/100 g) |
|---|---|---|---|---|---|---|---|---|---|
| Working Example | 1-1 | A1 | flat elliptical | 2.3379 | 0.132 | 17.7 | 0.51 | 145.1 | 152.3 |
|  | 1-2 | A2 | flat elliptical | 2.8614 | 0.200 | 14.3 | 0.32 | 133.6 | 141.7 |
|  | 1-3 | A3 | flat elliptical | 4.1451 | 0.833 | 4.98 | 0.17 | 101.2 | 106.1 |
|  | 1-4 | A4 | flat elliptical | 3.5076 | 0.133 | 26.4 | 0.31 | 184.6 | 192.8 |
|  | 1-5 | A5 | flat elliptical | 3.1547 | 0.357 | 8.84 | 0.28 | 92.8 | 98.4 |
|  | 1-6 | A6 | flat elliptical | 2.5137 | 0.217 | 11.56 | 0.26 | 81.9 | 100.3 |
|  | 1-7 | A7 | flat elliptical | 2.7458 | 0.139 | 19.8 | 0.41 | 82.7 | 104.5 |

TABLE 2-continued

|  | Polymer particle | Main shape | SB (m²/g) | SD (m²/g) | SB/SD | Bulk density (g/mL) | Water absorption (g/100 g) | Oil absorption (g/100 g) |
|---|---|---|---|---|---|---|---|---|
| Comparative Example 1-1 | B1 | elliptical/needle-shaped | 2.1234 | 0.385 | 5.52 | 0.34 | 91.4 | 94.4 |
| 1-2 | B2 | elliptical/needle-shaped | 1.5236 | 0.167 | 9.12 | 0.39 | 89.6 | 91.4 |
| 1-3 | B3 | spherical | 1.0374 | 1.000 | 1.04 | 0.72 | 57.9 | 53.3 |
| 1-4 | B4 | spherical | 0.0524 | 0.050 | 1.05 | 0.78 | 49.3 | 48.6 |

[Evaluation Test 1] Sensory Tests and Evaluation of Adhesion

Evaluations of feel, slip characteristics and particle adhesion were carried out by the methods described below on Polymer Particles A1 to A3 and B1 to B4 produced in Working Examples 1-1 to 1-3 and Comparative Examples 1-1 to 1-4, all of which were composed of the same ingredient. The results are shown in Table 3.

(1) Feel:

The tactile feel of each type of particle when spread over the skin was rated according to the criteria shown below.

(2) Slip Characteristics:

One gram of each type of particle was placed on black synthetic leather and the length when spread with a finger was rated according to the criteria shown below.

(3) Particle Adhesion:

One gram of each type of particle was placed on black synthetic leather and uniformly spread with a powder puff, following which the leather was struck three times and the amount of particles remaining was examined with a digital microscope (VHX200, from Keyence Corporation) and rated according to the criteria shown below.

⊚: excellent
○: good
Δ: standard
x: unacceptable

TABLE 3

|  | Polymer particle | Ingredient | Main shape | MV (μm) | Feel | Slip characteristics | Particle adhesion |
|---|---|---|---|---|---|---|---|
| Working Example 1-1 | A1 | methyl methacrylate | flat elliptical | 38 | ○ | ○ | ○ |
| 1-2 | A2 | methyl methacrylate | flat elliptical | 25 | ⊚ | ○ | ⊚ |
| 1-3 | A3 | methyl methacrylate | flat elliptical | 6 | ⊚ | ○ | ⊚ |
| Comparative Example 1-1 | B1 | methyl methacrylate | elliptical/needle-shaped | 13 | ○ | ○ | Δ |
| 1-2 | B2 | methyl methacrylate | elliptical/needle-shaped | 30 | Δ | ○ | Δ |
| 1-3 | B3 | methyl methacrylate | spherical | 5 | Δ | ○ | X |
| 1-4 | B4 | methyl methacrylate | spherical | 100 | ○ | ○ | X |

As shown in Table 3, with regard to feel and slip characteristics, the flat elliptical polymer particles were at least comparable to polymer particles lacking a flat region. With regard to particle adhesion, the flat elliptical polymer particles were far superior to polymer particles lacking a flat region.

[Evaluation Test 2] Heat Resistance Test on Crosslinked Particles

Evaluations of heat resistance were carried out by the following method on Polymer Particles A5 (crosslinked particle), A6 (crosslinked particle), A7 (crosslinked particle), B1 and B3 produced in Working Examples 1-5, 1-6 and 1-7 and Comparative Examples 1-1 and 1-3.

(4) Heat Resistance

An amount of 0.5 g of the respective particles was placed in an aluminum Petri dish and heated for 2 hours in a drying oven under the conditions shown in Table 4, following which the particles were visually checked for melting, the shape of the particles was identified by SEM examination, and evaluations of each were carried out based on the following criteria. The evaluation results are presented in Table 4.

Visual Evaluation
○: No major change
Δ: Partially melted
x: Melted

SEM Examination
1: Shapes are those of prepared particles
2: Shape of some particles retained
3: Shapes of prepared particles absent

TABLE 4

| | | Polymer particle | Ingredients | Heating conditions | | | | | | | | | |
|---|---|---|---|---|---|---|---|---|---|---|---|---|---|
| | | | | 80° C., 2 hours | | 100° C., 2 hours | | 120° C., 2 hours | | 150° C., 2 hours | | 200° C., 2 hours | |
| | | | | Visual | SEM | Visual | SEM | Visual | SEM | Visual | SEM | Visual | SEM |
| Working Example | 1-5 | A5 | methyl methacrylate ethylene glycol dimethacrylate | ○ | 1 | ○ | 1 | ○ | 1 | ○ | 1 | ○ | 1 |
| | 1-6 | A6 | methyl methacrylate ethylene glycol dimethacrylate | ○ | 1 | ○ | 1 | ○ | 1 | ○ | 1 | ○ | 1 |
| | 1-7 | A7 | methyl methacrylate glycidyl methacrylate | ○ | 1 | ○ | 1 | ○ | 1 | ○ | 1 | ○ | 1 |
| Comparative Example | 1-1 | B1 | methyl methacrylate | ○ | 1 | Δ | 2 | Δ | 2 | X | 3 | X | 3 |
| | 1-3 | B3 | methyl methacrylate | ○ | 1 | Δ | 2 | Δ | 2 | X | 3 | X | 3 |

[Evaluation Test 3] Chemical Resistance Test on Crosslinked Particles

Evaluations of chemical resistance were carried out by the following method on Polymer Particles A5 (crosslinked particle), A6 (crosslinked particle), A7 (crosslinked particle), B1 and B3 produced in Working Examples 1-5, 1-6 and 1-7 and Comparative Examples 1-1 and 1-3.

(5) Chemical Resistance

One gram of the respective particles and 99 g of the solvent indicated in Table 5 (particle concentration, 1 wt %) were stirred in a 300 mL flask for 30 minutes at 27° C. (300 K), following which the dispersed state of the particles was visually checked, the shape of the particles was identified by SEM examination, and evaluations of each were carried out based on the following criteria. The evaluation results are presented in Table 5. In Table 5, DMF stands for dimethylformamide, MEK stands for methyl ethyl ketone, and DPG stands for dipropylene glycol (the same applies below).

Visual Evaluation
○: Dispersed
Δ: Partially dispersed
x: Dissolved

SEM Examination
1: Shapes are those of prepared particles
2: Some deformation
3: Shapes of prepared particles absent

TABLE 5

| | | Polymer particle | Ingredients | Solvent | | | | | | | | | |
|---|---|---|---|---|---|---|---|---|---|---|---|---|---|
| | | | | Water | | Methanol | | Ethanol | | Ethyl acetate | | DMF | |
| | | | | Visual | SEM | Visual | SEM | Visual | SEM | Visual | SEM | Visual | SEM |
| Working Example | 1-5 | A5 | methyl methacrylate ethylene glycol dimethacrylate | ○ | 1 | ○ | 1 | ○ | 1 | ○ | 1 | ○ | 1 |
| | 1-6 | A6 | methyl methacrylate ethylene glycol dimethacrylate | ○ | 1 | ○ | 1 | ○ | 1 | ○ | 1 | ○ | 1 |
| | 1-7 | A7 | methyl methacrylate glycidyl methacrylate | ○ | 1 | ○ | 1 | ○ | 1 | ○ | 1 | ○ | 1 |
| Comparative Example | 1-1 | B1 | methyl methacrylate | ○ | 1 | Δ | 2 | Δ | 2 | X | 3 | X | 3 |
| | 1-3 | B3 | methyl methacrylate | ○ | 1 | Δ | 2 | Δ | 2 | X | 3 | X | 3 |

| | | Polymer particle | Ingredients | Solvent | | | | | | | |
|---|---|---|---|---|---|---|---|---|---|---|---|
| | | | | MEK | | DPG | | Acetone | | Toluene | |
| | | | | Visual | SEM | Visual | SEM | Visual | SEM | Visual | SEM |
| Working Example | 1-5 | A5 | methyl methacrylate ethylene glycol dimethacrylate | ○ | 1 | ○ | 1 | ○ | 1 | ○ | 1 |
| | 1-6 | A6 | methyl methacrylate ethylene glycol dimethacrylate | ○ | 1 | ○ | 1 | ○ | 1 | ○ | 1 |

TABLE 5-continued

|  |  |  | Ingredients |  |  |  |  |  |  |  |  |
|---|---|---|---|---|---|---|---|---|---|---|---|
|  | 1-7 | A7 | methyl methacrylate glycidyl methacrylate | ○ | 1 | ○ | 1 | ○ | 1 | ○ | 1 |
| Comparative Example | 1-1 | B1 | methyl methacrylate | X | 3 | Δ | 2 | X | 3 | X | 3 |
|  | 1-3 | B3 | methyl methacrylate | X | 3 | Δ | 2 | X | 3 | X | 3 |

[Evaluation Test 4] Hot Chemical Resistance Test on Cross-linked Particles

Evaluations of hot chemical resistance were carried out by the following method on Polymer Particles A5 (crosslinked particle), A6 (crosslinked particle), A7 (crosslinked particle), B1 and B3 produced in Working Examples 1-5, 1-6 and 1-7 and Comparative Examples 1-1 and 1-3.

(6) Hot Chemical Resistance

One gram of the respective particles and 99 g of the solvent indicated in Table 6 (particle concentration, 1 wt %) were stirred in a 300 mL flask for two hours at 70° C., following which the dispersed state of the particles was visually checked, the shape of the particles was identified by SEM examination, and evaluations of each were carried out based on the following criteria. The evaluation results are presented in Table 6.

Visual Evaluation
○: Dispersed
Δ: Partially dispersed
x: Dissolved

SEM Examination
1: Shapes are those of prepared particles
2: Some deformation
3: Shapes of prepared particles absent

TABLE 6

|  |  |  |  | Solvent |  |  |  |  |  |  |  |
|---|---|---|---|---|---|---|---|---|---|---|---|
|  |  |  |  | Water |  | Ethanol |  | Ethyl acetate |  | DMF |  |
|  |  | Polymer particle | Ingredients | Visual | SEM | Visual | SEM | Visual | SEM | Visual | SEM |
| Working Example | 1-5 | A5 | methyl methacrylate ethylene glycol dimethacrylate | ○ | 1 | ○ | 1 | ○ | 1 | ○ | 1 |
|  | 1-6 | A6 | methyl methacrylate ethylene glycol dimethacrylate | ○ | 1 | ○ | 1 | ○ | 1 | ○ | 1 |
|  | 1-7 | A7 | methyl methacrylate glycidyl methacrylate | ○ | 1 | ○ | 1 | ○ | 1 | ○ | 1 |
| Comparative Example | 1-1 | B1 | methyl methacrylate | ○ | 1 | Δ | 2 | X | 3 | X | 3 |
|  | 1-3 | B3 | methyl methacrylate | ○ | 1 | Δ | 2 | X | 3 | X | 3 |

|  |  |  |  | Solvent |  |  |  |  |  |
|---|---|---|---|---|---|---|---|---|---|
|  |  |  |  | MEK |  | DPG |  | Toluene |  |
|  |  | Polymer particle | Ingredients | Visual | SEM | Visual | SEM | Visual | SEM |
| Working Example | 1-5 | A5 | methyl methacrylate ethylene glycol dimethacrylate | ○ | 1 | ○ | 1 | ○ | 1 |
|  | 1-6 | A6 | methyl methacrylate ethylene glycol dimethacrylate | ○ | 1 | ○ | 1 | ○ | 1 |
|  | 1-7 | A7 | methyl methacrylate glycidyl methacrylate | ○ | 1 | ○ | 1 | ○ | 1 |

TABLE 6-continued

| | | | | | | | | | | |
|---|---|---|---|---|---|---|---|---|---|---|
| Comparative Example | 1-1 | B1 | methyl methacrylate | X | 3 | X | 3 | X | 3 |
| | 1-3 | B3 | methyl methacrylate | X | 3 | X | 3 | X | 3 |

As shown in Tables 4 to 6, the crosslinked flat elliptical polymer particles produced in Working Examples 1-5, 1-6 and 1-7 also had heat resistance, chemical resistance and hot chemical resistance while retaining the characteristics of their flat elliptical shape, thus demonstrating that use in applications requiring these properties is also possible.

[2] Preparation and Evaluation of Optical Measurement Dispersions

Working Example 2-1

Polymer Particle Dispersion 1 having a concentration of 0.1 wt % was prepared by mixing together 0.015 g of Polymer Particle A1 produced in Working Example 1-1 and 14.985 g of purified water.

Working Examples 2-2 to 2-7, Comparative Examples 2-1 to 2-4

Aside from changing Polymer Particle A1 to, respectively, Polymer Particles A2 to A7 and B1 to B4, Polymer Particle Dispersions 2 to 11 having a concentration of 0.1 wt % were prepared in the same way as in Working Example 2-1.

[Evaluation Test 5]

Using a UV-visible spectrophotometer (UV-2450, from JASCO Corporation; referred to below as the "UV-visible spectrophotometer"), Dispersions 1 to 11 were poured into respective quartz cells furnished with the spectrophotometer and transmitted light analysis on the dispersed particles was carried out at wavelengths of 360 nm, 500 nm, 600 nm and 700 nm. The results are shown in Table 7.

As is apparent from Table 7, the dispersions in Working Examples 2-1 to 2-7 in which the flat elliptical polymer particles produced in Working Examples 1-1 to 1-7 were used had better light-diffusing effects than the dispersions in Comparative Examples 2-1 to 2-4 in which polymer particles lacking a flat region were used.

[3] Preparation and Evaluation of Optical Measurement Sheets

Working Example 3-1

A composition for optical measurement sheets was prepared by mixing together 15.0 g of the Polymer Particle A1 obtained in Working Example 1-1, 35.0 g of binder resin (a PVA resin from Kuraray Co., Ltd.) and 75.0 g of purified water. This composition was coated onto one side of a 100 μm thick PET film (E-5000, from Toyobo Co., Ltd.) using a commercial bar coater, following which a drying oven was set to 60° C. and forced hot-air drying was carried out for 20 minutes, thereby producing Optical Sheet 1 in which the applied layer had a thickness of 40 μm.

Working Examples 3-2 to 3-7, Comparative Examples 3-1 to 3-4

Aside from changing Polymer Particle A1 to Polymer Particles A2 to A7 and B1 to B4, compositions and Optical Sheets 2 to 11 were prepared in the same way as in Working Example 3-1.

[Evaluation Test 6]

Using a UV-visible spectrophotometer, transmitted light analysis at wavelengths of 360 nm, 500 nm, 600 nm and 700 nm was carried out on Optical Sheets 1 to 11. The results are shown in Table 8.

TABLE 7

| | | Polymer | | | Transmittance (%) | | | |
|---|---|---|---|---|---|---|---|---|
| | | dispersion | Ingredients | Main shape | 360 nm | 500 nm | 600 nm | 700 nm |
| Working Example | 2-1 | 1 | methyl methacrylate | flat elliptical | 2.1 | 2.4 | 2.6 | 2.9 |
| | 2-2 | 2 | methyl methacrylate | flat elliptical | 1.9 | 2.3 | 2.6 | 2.8 |
| | 2-3 | 3 | methyl methacrylate | flat elliptical | 0.4 | 0.6 | 0.7 | 0.8 |
| | 2-4 | 4 | styrene 2-hydroxyethyl methacrylate | flat elliptical | 1.5 | 1.6 | 1.8 | 2.0 |
| | 2-5 | 5 | methyl methacrylate ethylene glycol dimethacrylate | flat elliptical | 0.3 | 0.4 | 0.5 | 0.7 |
| | 2-6 | 6 | methyl methacrylate ethylene glycol dimethacrylate | flat elliptical | 0.9 | 1.2 | 1.8 | 2.2 |
| | 2-7 | 7 | methyl methacrylate glycidyl methacrylate | flat elliptical | 1.7 | 1.9 | 2.4 | 2.7 |
| Comparative Example | 2-1 | 8 | methyl methacrylate | elliptical/needle-shaped | 3.2 | 4.4 | 5.8 | 7.2 |
| | 2-2 | 9 | methyl methacrylate | elliptical/needle-shaped | 5.6 | 6.3 | 7.7 | 8.2 |
| | 2-3 | 10 | methyl methacrylate | spherical | 10.4 | 9.1 | 8.5 | 8.3 |
| | 2-4 | 11 | methyl methacrylate | spherical | 23.6 | 22.4 | 21.5 | 21.4 |

TABLE 8

| | Optical sheet | | Ingredients | Main shape | Transmittance (%) | | | |
|---|---|---|---|---|---|---|---|---|
| | | | | | 360 nm | 500 nm | 600 nm | 700 nm |
| Working Example | 3-1 | 1 | methyl methacrylate | flat elliptical | 4.3 | 7.2 | 13.4 | 17.5 |
| | 3-2 | 2 | methyl methacrylate | flat elliptical | 2.8 | 5.6 | 9.7 | 15.1 |
| | 3-3 | 3 | methyl methacrylate | flat elliptical | 1.2 | 3.9 | 6.9 | 9.8 |
| | 3-4 | 4 | styrene 2-hydroxyethyl methacrylate | flat elliptical | 2.2 | 5.4 | 9.6 | 14.8 |
| | 3-5 | 5 | methyl methacrylate ethylene glycol dimethacrylate | flat elliptical | 1.5 | 4.6 | 8.3 | 12.5 |
| | 3-6 | 6 | methyl methacrylate ethylene glycol dimethacrylate | flat elliptical | 1.9 | 5.1 | 8.6 | 13.1 |
| | 3-7 | 7 | methyl methacrylate glycidyl methacrylate | flat elliptical | 3.0 | 6.4 | 10.7 | 16.8 |
| Comparative Example | 3-1 | 8 | methyl methacrylate | elliptical/needle-shaped | 9.4 | 16.9 | 25.6 | 37.4 |
| | 3-2 | 9 | methyl methacrylate | elliptical/needle-shaped | 10.2 | 18.7 | 31.4 | 41.6 |
| | 3-3 | 10 | methyl methacrylate | spherical | 31.4 | 42.8 | 54.2 | 63.4 |
| | 3-4 | 11 | methyl methacrylate | spherical | 45.8 | 52.4 | 60.8 | 67.3 |

As shown in Table 8, with optical sheets as well, better light-diffusing effects were obtained when flat elliptical polymer particles were used (Working Examples 3-1 to 3-7) than when polymer particles lacking a flat region were used (Comparative Examples 3-1 to 3-4). Also, in the optical sheets produced in Working Examples 3-1 to 3-7, the light-scattering effects were high in the UV to visible light range, and so these sheets also had an excellent hiding power.

[4] Preparation and Evaluation of Skin-Cleansing Compositions

Working Example 4-1 and Comparative Examples 4-1 and 4-2

Skin-cleaning compositions (Cleansing Compositions 1 to 3) formulated as shown in Table 9 below were prepared using Polymer Particles A1, B1 and B3 obtained in Working Example 1-1 and Comparative Examples 1-1 and 1-3.

TABLE 9

| | | Working Example 4-1 Cleansing Composition 1 | Comparative Example 4-1 Cleansing Composition 2 | Comparative Example 4-2 Cleansing Composition 3 |
|---|---|---|---|---|
| Amount (g) | Stearic acid | 2.0 | 2.0 | 2.0 |
| | Palmitic acid | 4.0 | 4.0 | 4.0 |
| | Myristic acid | 10.0 | 10.0 | 10.0 |
| | Lauric acid | 3.0 | 3.0 | 3.0 |
| | Lauramidopropylamine oxide | 20.0 | 20.0 | 20.0 |
| | Polypropylene glycol (400) | 2.0 | 2.0 | 2.0 |
| | Triethanolamine | 14.0 | 14.0 | 14.0 |
| | Ethylene glycol distearate | 1.0 | 1.0 | 1.0 |
| | Purified water | 41.0 | 41.0 | 41.0 |
| | Polymer Particle A1 | 3.0 | — | — |
| | Polymer Particle B1 | — | 3.0 | — |
| | Polymer Particle B3 | — | — | 3.0 |

[Evaluation Test 7]

Using an automated goniophotometer (GP-200, from Murakami Color Research Laboratory Co., Ltd.), the same Optical Sheets 3, 8 and 10 produced in Working Example 3-3 and Comparative Examples 3-1 and 3-3 using particles all made of the same ingredients were irradiated with a fixed amount of light at an incident angle of 45° and the light scattering distribution of reflected light was measured. The results are shown in FIG. 6.

The results in FIG. 6 demonstrate that better reflected light scattering effects are obtained with flat elliptical polymer particles than with spherical polymer particles and even elliptical polymer particles lacking a flat region.

[Evaluation Test 8]

Evaluations were carried out by the following methods on the cleansing compositions prepared. The results are shown in Table 10.

Ten people were selected as panelists, usage tests in which the panelists washed their faces using the skin cleansing composition were carried out, and the following six qualities were each evaluated according to the criteria indicated below: Feeling on Use 1, Feeling on Use 2, Foamability, Skin Scrubbing/Exfoliating Effect, Massaging Effects, and Irritation. Based on these results, an overall evaluation of the composition as a scrub was carried out.
[Feeling on Use 1] Degree to which cleanser is pleasant to apply and penetrates skin during use.
[Feeling on Use 2] Degree to which there is no sense of residual scrub or tautness of skin after rinsing off cleanser.
[Foamability] Degree of foamability and foam durability during use of cleanser.

[Skin Scrubbing/Exfoliating Effect] Degree to which cosmetics come off after use.

[Massaging Effects] Are massaging effects such as alleviation of skin dullness, improved complexion and promotion of blood circulation apparent after cleansing?

[Irritation] Degree to which redness and tingling after cleanser has been rinsed off are absent.

[Evaluation Criteria for Each Quality]

⊚: Clearly effective (good sensation) [assessed highly by 8 or more panelists]

◯: Effective (somewhat good sensation) [assessed highly by 6 or 7 panelists]

☐: Effective (somewhat good sensation) [assessed highly by 4 or 5 panelists]

Δ: Not very effective (somewhat poor sensation) [assessed highly by 2 or 3 panelists]

x: Ineffective (poor sensation) [assessed highly by 1 or no panelists]

[Scoring]
- ⊚: 8 points
- ◯: 6 points
- ☐: 4 points
- Δ: 2 points
- x: 0 points

[Overall Evaluation]
- A: 37 points or more
- B: 25 to 36 points
- C: 13 to 24 points
- D: 12 points or less

TABLE 10

|  | Working Example 4-1 Cleansing Composition 1 | Comparative Example 4-1 Cleansing Composition 2 | Comparative Example 4-2 Cleansing Composition 3 |
|---|---|---|---|
| Feeling on Use 1 | ⊚ | ◯ | Δ |
| Feeling on Use 2 | ◯ | ◯ | ◯ |
| Foamability | ◯ | ◯ | Δ |
| Skin Scrubbing/ Exfoliating Effect | ◯ | ◯ | Δ |
| Massaging Effects | ⊚ | ◯ | Δ |
| Irritation | ◯ | ◯ | ◯ |
| Score | 40 | 36 | 20 |
| Overall evaluation as a scrub | A | B | C |

The results in Table 10 demonstrate that flat elliptical polymer particles are useful as an additive (ingredient) for body cleansing compositions.

[5] Preparation and Evaluation of Make-Up Compositions

Working Examples 5-1 and 5-2, and Comparative Examples 5-1 and 5-2

Make-up compositions (Foundation 1 to 4) formulated as shown in Table 11 below were prepared using Polymer Particles A2, A3, B2 and B3 obtained in Working Example 1-2, Working Example 1-3 and Comparative Examples 1-2 and 1-3.

TABLE 11

|  |  | Working Example 5-1 Foundation 1 | Working Example 5-2 Foundation 2 | Comparative Example 5-1 Foundation 3 | Comparative Example 5-2 Foundation 4 |
|---|---|---|---|---|---|
| Amount (g) | Red iron oxide | 0.4 | 0.4 | 0.4 | 0.4 |
|  | Yellow iron oxide | 1.0 | 1.0 | 1.0 | 1.0 |
|  | Black iron oxide | 0.2 | 0.2 | 0.2 | 0.2 |
|  | Titanium oxide | 7.0 | 7.0 | 7.0 | 7.0 |
|  | Zinc oxide | 3.0 | 3.0 | 3.0 | 3.0 |
|  | Silicone-treated large particle-size titanium oxide | 3.0 | 3.0 | 3.0 | 3.0 |
|  | Lauroyl lysine powder | 14.0 | 14.0 | 14.0 | 14.0 |
|  | Titanium-mica powder | 4.0 | 4.0 | 4.0 | 4.0 |
|  | Talc | 35.97 | 35.97 | 35.97 | 35.97 |
|  | Methyl phenyl polysiloxane | 2.0 | 2.0 | 2.0 | 2.0 |
|  | Crystalline cellulose | 5.0 | 5.0 | 5.0 | 5.0 |
|  | Cornstarch | 10.0 | 10.0 | 10.0 | 10.0 |
|  | Methyl paraben | 0.1 | 0.1 | 0.1 | 0.1 |
|  | Sodium dehydroacetate | 0.1 | 0.1 | 0.1 | 0.1 |
|  | Liquid paraffin | 1.5 | 1.5 | 1.5 | 1.5 |
|  | Butylene glycol | 0.5 | 0.5 | 0.5 | 0.5 |
|  | Job's tears extract | 0.1 | 0.1 | 0.1 | 0.1 |
|  | Ginseng root extract | 0.1 | 0.1 | 0.1 | 0.1 |
|  | Ubiquinone | 0.03 | 0.03 | 0.03 | 0.03 |
|  | Polymer Particle A2 | 12.0 | — | — | — |
|  | Polymer Particle A3 | — | 12.0 | — | — |
|  | Polymer Particle B2 | — | — | 12.0 | — |
|  | Polymer Particle B3 | — | — | — | 12.0 |

[Evaluation Test 9]

Ten people were selected as panelists, and the feel during use and difference before and after use for Foundations 1 to 4 were evaluated overall in terms of the following five qualities: "adhesion to skin," "sense of fit when applied," "sensation during use," "soft focus effect" and "durability of cosmetic effect (4 hours)," based on which the acceptability of the cosmetic formulation was rated as A to E below.

A: Foundation 1 was best
B: Foundation 2 was best
C: Foundation 3 was best
D: Foundation 4 was best
E: They were all the same.

As a result, the assessments by the panelists were as follows:

A: 3 panelists
B: 4 panelists
C: 3 panelists
D: 0 panelists
E: 0 panelists

Moreover, many of the panelists thought that Foundations 1 and 2 were particularly outstanding with respect to the "adhesion to skin," "soft focus effect" and "durability of cosmetic effect (4 hours)," and that the overall finish was good. Also, many of the panelists thought that Foundation 3 had a sensation during use and a finish that were similar to those of Foundations 1 and 2. On the other hand, many of the panelists thought that Foundation 4 lacked "adhesion to skin" and "durability of cosmetic effect (4 hours)."

The above results demonstrate that the flat elliptical polymer particles obtained by the production method of the invention have little extraneous matter such as agglomerates and can be stably and efficiently produced, and moreover that crosslinked particles also can be stably produced, thus enabling such particles to be utilized in various applications. Because flat elliptical polymer particles, in addition to retaining the properties inherent to elliptical polymer particles, also have a variety of properties by virtue of their flat shape, they can be effectively used in applications for which polymer particles are required, such as paints, inks, molded or formed articles, cosmetics, and thermally cavitated products having pores.

The invention claimed is:

1. A flat elliptical polymer particle which has, in projections based on the third-angle projection method, a front view, a plan view and a side view that are all elliptical and which satisfies conditions (1) to (4) below:
   (1) a flat region of the particle has an average length $L_{AV}$ such that $0.13 \leq L_{AV} \leq 500$ μm,
   (2) a flat region of the particle has an average breadth $D_{AV}$ such that $0.1 \leq D_{AV} \leq 250$ μm,
   (3) the aspect ratio L/D calculated from the length L and breadth D has an average value $P1_{AV}$ such that $1.3 < P1_{AV} \leq 50$, and
   (4) the aspect ratio D/T calculated from the breadth D and a lateral face thickness T has an average value $P2_{AV}$ such that $1.2 < P2_{AV} \leq 100$,
   wherein the flat elliptical polymer particle has a water absorption of at least 60 mL per 100 g of particles and/or an oil absorption of at least 60 mL per 100 g of particles.

2. The flat elliptical polymer particle of claim 1 which is obtained by solution polymerization (exclusive of seed polymerization).

3. The flat elliptical polymer particle of claim 1 which further satisfies condition (5) below:
   (5) the aspect ratio L/T calculated from the length L and the thickness T has an average value $P3_{AV}$ such that $1.56 < P3_{AV} \leq 150$.

4. The flat elliptical polymer particle of claim 1 which comprises, attached to or included within at least a surface or a surface layer portion thereof, a fine particle that satisfies condition (6) below:
   (6) the fine particle attached to or included within the particle surface or surface layer portion has a particle size SP such that $\frac{1}{1,000} \times D_{AV} \leq SP \leq \frac{1}{2} \times D_{AV}$.

5. The flat elliptical polymer particle of claim 4 which has an uneven surface shape owing to the fine particle.

6. The flat elliptical polymer particle of claim 1, wherein the ratio SB/SD between the actual specific surface area SB of the flat elliptical polymer particle and the theoretical specific surface area SD of a spherical particle calculated from the volume mean particle size of the flat elliptical polymer particle satisfies the condition SB/SD 1.2.

7. The flat elliptical polymer particle of claim 1 which has a bulk density of from 0.01 to 0.7 g/mL.

8. The flat elliptical polymer particle of claim 1 which is a crosslinked polymer particle.

9. The flat elliptical polymer particle of claim 8 which has a heat resistance of at least 100° C.

10. A resin composition obtained using the flat elliptical polymer particle of claim 1.

11. A light-diffusing sheet obtained using the flat elliptical polymer particle of claim 1.

12. A paint composition obtained using the flat elliptical polymer particle of claim 1.

13. An ink composition obtained using the flat elliptical polymer particle of claim 1.

14. A cosmetic preparation obtained using the flat elliptical polymer particle of claim 1.

15. A material for the electrical or electronics industry obtained using the flat elliptical polymer particle of claim 1.

16. An adhesive obtained using the flat elliptical polymer particle of claim 1.

17. A thermally cavitated product having pores obtained using the flat elliptical polymer particle of claim 1.

18. A diagnostic agent for medical use obtained using the flat elliptical polymer particle of claim 1.

19. A method for producing the flat elliptical polymer particle of claim 1 by solution polymerizing an unsaturated monomer in a solvent and in the presence of a polymerization initiator, wherein the solvent is a mixed solvent of water, a hydrophilic organic solvent and a hydrophobic organic solvent, and
   the polymerization initiator is used as one type that dissolves in at least one of the water, the hydrophilic organic solvent and the hydrophobic organic solvent, or is used as a combination of two or more types that dissolves in each of the water, the hydrophilic organic solvent and the hydrophobic organic solvent.

20. The flat elliptical polymer particle production method of claim 19, wherein the unsaturated monomer is at least one selected from the group consisting of styrenic monomers, (meth)acrylic acids, (meth)acrylic ester monomers and vinyl ester monomers.

21. The flat elliptical polymer particle production method of claim 19, wherein the unsaturated monomer includes an unsaturated monomer that is liquid at 25° C. and hydrophobic, and
   the ratio of hydrophobic liquid ingredients, including the hydrophobic liquid unsaturated monomer and the hydrophobic organic solvent, relative to the total weight of charged ingredients, is set to at least 10 wt %.

22. The flat elliptical polymer particle production method of claim 19, wherein the polymerization initiator is a combination of at least one type of water-soluble initiator and at least one type of oil-soluble initiator.

23. The flat elliptical polymer particle production method of claim 19, wherein the hydrophobic organic solvent is an organic compound having a molecular weight of at least 200.

24. The flat elliptical polymer particle production method of claim 21, wherein the hydrophobic organic solvent has an ability to dissolve the hydrophobic liquid unsaturated monomer and does not have an ability to dissolve flat elliptical polymer particles that form in the polymerization reaction.

* * * * *